United States Patent
Inoue et al.

(10) Patent No.: US 7,142,976 B2
(45) Date of Patent: Nov. 28, 2006

(54) ABNORMALITY DIAGNOSIS METHOD AND APPARATUS FOR GAS CONCENTRATION MEASURING DEVICE

(75) Inventors: Yoshinori Inoue, Aichi (JP); Norikazu Ieda, Aichi (JP); Masahiro Tanaka, Aichi (JP); Reina Kito, Nagoya (JP); Keigo Banno, Aichi (JP); Tatsuki Hirabayashi, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 11/167,163

(22) Filed: Jun. 28, 2005

(65) Prior Publication Data

US 2005/0288847 A1  Dec. 29, 2005

(30) Foreign Application Priority Data

Jun. 29, 2004 (JP) ............................. 2004-191722

(51) Int. Cl.
*G06F 19/00* (2006.01)
*F02D 41/14* (2006.01)
*G01N 27/26* (2006.01)

(52) U.S. Cl. .................. 701/114; 701/109; 12/688; 204/401

(58) Field of Classification Search ........ 701/101–103, 701/109, 114; 123/688, 690; 204/401, 424–426; 73/23.31, 23.32
See application file for complete search history.

(56) References Cited

U.S. PATENT DOCUMENTS

| | | | | | |
|---|---|---|---|---|---|
| 4,724,814 A | * | 2/1988 | Mieno et al. | ............... | 123/688 |
| 4,724,815 A | * | 2/1988 | Mieno et al. | ............... | 123/690 |
| 4,777,922 A | * | 10/1988 | Mieno et al. | ............... | 123/688 |
| 4,819,602 A | * | 4/1989 | Mieno et al. | ............... | 123/688 |
| 5,020,499 A | * | 6/1991 | Kojima et al. | ............. | 204/401 |
| 5,209,206 A | * | 5/1993 | Danno et al. | ............... | 123/688 |
| 5,340,462 A | * | 8/1994 | Suzuki | ....................... | 204/425 |
| 6,136,169 A | * | 10/2000 | Okamoto | ................... | 204/401 |
| 6,812,436 B1 | * | 11/2004 | Nomura et al. | ............. | 219/497 |
| 7,073,320 B1 | * | 7/2006 | Moritsugu et al. | .......... | 123/688 |
| 2004/0238378 A1 | * | 12/2004 | Kumazawa et al. | ........ | 204/401 |

FOREIGN PATENT DOCUMENTS

JP         2003-90821         3/2003

* cited by examiner

*Primary Examiner*—Willis R. Wolfe, Jr.
(74) *Attorney, Agent, or Firm*—Sughrue Mion, PLLC

(57) ABSTRACT

An abnormality diagnosis method for a gas concentration measuring device, includes electrically shutting off measurement means from an oxygen concentration detecting cell and an oxygen pump cell of a gas sensor when a voltage at one of electrical connection points through which the measurement means is electrically connected to the oxygen concentration detecting cell and the oxygen pump cell becomes equal to a predetermined abnormal voltage value, and thereafter, electrically connecting the measurement means to the oxygen concentration detecting cell and the oxygen pump cell of the gas sensor to perform an abnormality diagnosis of the gas sensor. An abnormality diagnosis apparatus for a gas concentration measuring device is also provided.

22 Claims, 9 Drawing Sheets

FIG.3

| OPERATION MODE | SWITCH | | | | | | |
|---|---|---|---|---|---|---|---|
| | SW1 | SW2 | SW3 | SW4 | SW5 | SW6 | SW7 |
| GAS CONCENTRATION MEASUREMENT MODE | OFF | ON | ON | OFF | OFF | OFF | ON |
| PROTECTION MODE | OFF | OFF | OFF | OFF | OFF | OFF | OFF |
| ABNORMALITY DIAGNOSIS MODE | ON | OFF | OFF | ON | OFF | ON | OFF |
| REFERENCE OXYGEN RECOVERY MODE | OFF | OFF | OFF | OFF | ON | ON | OFF |

FIG.4

| KIND OF ABNORMALITY | TERMINAL | DETERMINATION CONDITIONS |
|---|---|---|
| GND SHORT | Vs+ | Vs+ VOLTAGE < COM VOLTAGE AND Vs+ VOLTAGE < Ip+ VOLTAGE |
| | COM | RELATION OTHER THAN DESCRIBED ABOVE AND BELOW |
| | Ip+ | Ip+ VOLTAGE < COM VOLTAGE AND Ip+ VOLTAGE < Vs+ VOLTAGE |
| VB SHORT | Vs+ | Vs+ VOLTAGE > COM VOLTAGE AND Vs+ VOLTAGE > Ip+ VOLTAGE |
| | COM | RELATION OTHER THAN DESCRIBED ABOVE AND BELOW |
| | Ip+ | Ip+ VOLTAGE > COM VOLTAGE AND Ip+ VOLTAGE > Vs+ VOLTAGE |

ABNORMALITY DIAGNOSIS METHOD AND APPARATUS FOR GAS CONCENTRATION MEASURING DEVICE

BACKGROUND OF THE INVENTION

The present invention relates to an abnormality diagnosis method and apparatus for a gas concentration measuring device for use with an internal combustion engine for combustion control thereof.

Heretofore, in combustion control of an internal combustion engine such as a gasoline engine for reducing CO, NOx and HC contained in the exhaust gas through control of an air-fuel ratio of a mixture of air and fuel to be supplied to the internal combustion engine, there is known such a method of feedback controlling a fuel supply amount in accordance with a concentration of a predetermined gas component contained in an exhaust gas.

As a sensor used for such an air-fuel ratio control, there is known a wide-range air-fuel ratio sensor (also referred to as a UEGO sensor) in which two cells with electrodes are disposed on the opposite sides of a solid electrolytic body made of a material containing zirconia or the like as a major component in a way as to place therebetween a measurement chamber and a measured gas is introduced into the measurement chamber by way of a diffusion resistor for measuring an oxygen concentration in the measured gas, a NOx sensor which is provided with another cell in addition to the above-described two cells so as to be capable of detecting a NOx concentration.

The sensors such as a UEGO sensor can detect a concentration of a predetermined gas component in an exhaust gas over a wide range continuously and thereby improve the accuracy in the combustion control, thus being used widely in these years.

Further, in recent vehicles is used a gas concentration measuring device that performs, during combustion control of an engine using such a gas sensor, an abnormality diagnosis of the gas sensor or a gas sensor controller automatically (a so-called onboard self-diagnosis) and informing a driver of the result of diagnosis.

As such an abnormality diagnosis method of a gas concentration measuring device, there is heretofore known, as disclosed in Japanese Patent Provisional Publication (unexamined) No. 2003-90821, a method of detecting input and output voltages at each electrode of a plurality of cells constituting a gas sensor, and determining whether or not the respective electrode voltages are abnormal for thereby performing an abnormality diagnosis of a short-circuit between a wiring electrically connected to a sensor element and a battery (power source potential), a short-circuit between the wiring and the ground (earth potential) or breakage of the wiring.

SUMMARY OF THE INVENTION

In the meantime, in the above-described abnormality diagnosis method, the gas concentration measuring device is adapted to keep operating even in the case of occurrence of a short-circuit or the like abnormality, thus causing a possibility that an excessively large, abnormal current flows through the sensor element to damage the same.

Further, the sensor element is composed of a plurality of cells that generate an electromotive force in accordance with the concentration of oxygen. For this reason, the electrode voltage of each cell is also varied in accordance with the concentration of oxygen of the measurement gas at the time of detection of the voltage. Accordingly, the above-described abnormality diagnosis method cannot determine or locate the position where the abnormality is caused though can determine the kind of abnormality caused.

It is accordingly an object of the present to provide an abnormality diagnosis method and apparatus for a gas concentration measuring device, which can decide or determine, in case of occurrence of an abnormality of the gas concentration measuring device, the kind of abnormality and the place where the abnormality is caused without damaging a gas sensor of the gas concentration measuring device.

To achieve the above object, there is provided according to an aspect of the present invention an abnormality diagnosis method for a gas concentration measuring device having a gas sensor and measurement means, the gas sensor having a measurement chamber in communication with a measured gas space by way of a diffusion resistor, an oxygen concentration detecting cell that produces a voltage in accordance with an oxygen concentration in the measurement chamber and an oxygen pump cell that pumps oxygen into or out of the measurement chamber in accordance with a current flowing therethrough, the oxygen concentration detecting cell having a solid electrolytic body and a pair of electrodes disposed in the solid electrolytic body, one of which electrodes faces the measurement chamber, the oxygen pump cell having a solid electrolytic body and a pair of electrodes disposed in the solid electrolytic body, one of which electrodes faces the measurement chamber, the measurement means being electrically connected to the oxygen concentration detecting cell and the oxygen pump cell for measuring the concentration of a predetermined gas component of a measure gas in the measured gas space by controlling a current flowing through the oxygen pump cell so that an output voltage of the oxygen concentration detecting cell is held at a constant value, the abnormality diagnosis method comprising electrically shutting off the measurement means from the oxygen concentration detecting cell and the oxygen pump cell of the gas sensor when a voltage at one of electrical connection points through which the measurement means is electrically connected to the oxygen concentration detecting cell and the oxygen pump cell of the gas sensor becomes equal to a predetermined abnormal voltage value, and thereafter, electrically connecting the measurement means to the oxygen concentration detecting cell and the oxygen pump cell of the gas sensor to perform an abnormality diagnosis of the gas sensor.

By the abnormality diagnosis method, when an abnormality is caused in the gas sensor and the voltage at one of the electrical connection points becomes equal to a predetermined abnormal voltage value, the measurement means is electrically shut off from the oxygen concentration detecting cell and the oxygen pump cell, and thereafter the abnormality diagnosis is performed. Thus, it becomes possible to prevent an abnormal current from flowing through the gas sensor subsequently after an abnormality is caused in the gas sensor and thereby prevent the gas sensor from being damaged.

According to another aspect of the present invention, there is provided an abnormality diagnosis method wherein the electrically connecting comprises supplying a predetermined current to the oxygen concentration detecting cell and the oxygen pump cell by way of the electrical connection points and performing the abnormality diagnosis on the basis of voltages of the respective electrical connection points that are detected at the time of supply of the predetermined current.

The abnormality diagnosis can be performed assuredly by supplying to the oxygen concentration detecting cell and the oxygen pumping cell such a predetermined current that causes at the electrical connection points voltages larger than those produced by the oxygen concentration detecting cell and the oxygen pumping cell produce in accordance with the oxygen concentration in the measured gas space. In this connection, by supplying a minimum current necessary for the abnormality diagnosis for a necessary time, the abnormality diagnosis can be performed assuredly without damaging the gas sensor.

In the meantime, there is a case in which though an abnormality is caused in the gas sensor, the abnormality is eliminated immediately thereafter. In such a case, if the abnormality diagnosis is performed immediately after the voltage at one of the connection points becomes equal to a predetermined abnormal voltage value and the measurement means is electrically shut off from the oxygen concentration detecting cell and the oxygen pumping cell, it means that an abnormality diagnosis is performed though the gas sensor is normal and therefore an unnecessary processing is executed. Furthermore, in case the abnormality diagnosis is performed by supplying a current to the gas sensor, it means that a current is supplied to the gas sensor though the gas sensor is normal and therefore the gas sensor may possibly be deteriorated by the unnecessary supply of current.

To solve such a problem, there is provided according to a further aspect of the present invention, an abnormality diagnosis method wherein the electrically connecting comprises applying a predetermined voltage to the electrically connection points, determining that the gas sensor is abnormal if one of voltages at the electrical connection points is a predetermined abnormal voltage value at the time of application of the predetermined voltage, and performing the abnormality diagnosis after it is determined that the gas sensor is abnormal.

By performing the abnormality diagnosis after the gas sensor is determined to be abnormal, it becomes possible to dispense with the abnormality diagnosis with respect to the normal gas sensor and therefore it becomes possible to prevent the process speed of the gas concentration measuring device, from being lowered. Further, it becomes possible to eliminate unnecessary supply of current to the normal gas sensor and prevent the gas sensor from being deteriorated.

The gas sensor is disposed, in many cases, in the place exposed to electrical noises by, for example, spark plugs within an engine compartment of an automotive vehicle. For this reason, it is known to provide the measurement means of the gas concentration measuring device with oscillation preventing means for preventing oscillation from being caused by the electrical noises. However, when the measurement means is provided with the oscillation preventing means, the voltages at the respective electrical connection points become unstable transiently after the measurement means is electrically shut off from the oxygen concentration detecting cell and the oxygen pumping cell.

Thus, there is provided according to a further aspect of the present invention an abnormality diagnosis method wherein the measurement means is electrically connected with oscillation preventing means for preventing an oscillation phenomenon caused by a current control of the oxygen pump cell, and wherein the electrically connecting comprises performing the abnormality diagnosis after lapse of a predetermined time during which by the oscillation preventing means, after the measurement means is electrically shut off from the oxygen concentration detecting cell and the oxygen pump cell of the gas sensor.

The abnormality diagnosis is thus performed after the unstable condition transiently caused by the oscillation preventing means after the gas sensor is electrically shut off from the connection points, i.e., from the measurement means, and therefore it becomes possible to perform an accurate abnormality diagnosis.

In the meantime, in the gas concentration detecting cell, it is necessary to introduce a gas of a known oxygen concentration to the electrode disposed outside the measurement chamber in order to form a reference oxygen atmosphere. To attain this end, there is known such a method of supplying a small constant current to the gas concentration detecting cell to form a reference oxygen atmosphere around the above-described electrode (the electrode is referred to as a self-generating reference electrode). It is assumed such a case in which an abnormality is caused in a gas sensor having such a structure, and in which it is determined by the abnormality diagnosis that the abnormality is of such a kind that a current flows in the direction to reduce the oxygen concentration around the self-generation reference electrode and thereafter the abnormality is eliminated. When this is the case, if the gas sensor is made to perform a usual operation immediately after the abnormality is eliminated, it takes a long time for the oxygen concentration around the self-generation reference electrode to increase up to a predetermined value since the current for pumping oxygen into a space around the self-generation reference electrode is small.

To solve such a problem, there is provided according to a further aspect of the present invention, an abnormality diagnosis method wherein the other of the electrodes of the oxygen concentration detecting cell is disposed outside the measurement chamber and in a state of being shut off from the outside and the measurement means includes constant current supply means for supplying a constant current to the oxygen concentration detecting cell in order to form a reference oxygen atmosphere of a constant oxygen concentration around the other of the electrodes of the oxygen concentration detecting cell, and wherein the electrically connecting comprises supplying to the oxygen concentration detecting cell a current that flows in the same direction as the constant current and that is larger than the constant current when an abnormality is eliminated after it is diagnosed by the abnormality diagnosis that there has occurred an abnormality that a current flows through the oxygen concentration detecting cell in the direction opposite to the constant current.

By this, in case an abnormality having been caused in the gas sensor is eliminated from some cause, measurement of a predetermined gas, concentration by the gas concentration measuring device can be restarted rapidly.

According to a further aspect of the present invention, there is provided an abnormality diagnosis apparatus for a gas concentration measuring device, comprising a gas sensor having a measurement chamber, an oxygen concentration detecting cell that produces a voltage in accordance with an oxygen concentration in the measurement chamber and an oxygen pump cell that pumps oxygen into or out of the measurement chamber in accordance with a current flowing therethrough, the measurement chamber being in communication with a measured gas space containing a measured gas by way of a diffusion resistor, the oxygen concentration detecting cell having a solid electrolytic body and a pair of electrodes disposed in the solid electrolytic body, one of which electrodes faces the measurement chamber, the oxygen pump cell having a solid electrolytic body and a pair of electrodes disposed in the solid electrolytic body, one of which electrodes faces the measurement chamber, measurement means electrically connected to the oxygen concentration detecting cell and the oxygen pump cell for measuring the concentration of a predetermined gas component of the measured gas by controlling a current flowing through the oxygen pump cell so that an output voltage of the oxygen concentration detecting cell is maintained at a constant value, determining means for determining whether a voltage at each of electrical connection points through which the measurement means is electrically connected to the oxygen concentration detecting cell and the oxygen pump cell is a predetermined abnormal voltage value, shut-off means for electrically shutting off the measurement means from the oxygen concentration detecting cell and the oxygen pump cell when it is determined by the determining means that a voltage at one of the electrical connection points is the predetermined abnormal voltage value, and abnormality diagnosis means for performing an abnormality diagnosis after the measurement means is electrically shut off from the oxygen concentration detecting cell and the oxygen pump cell by the shut-off means.

The abnormality diagnosis apparatus can produce substantially the same effect as described with respect to the abnormality diagnosis method.

BRIEF DESCRIPTION OF THE DRAWINGS

FIG. 3 is a view showing operating conditions of switches at various operation modes of a sensor element driving circuit of the electronic control unit;

FIG. 4 is a view showing determination conditions on the basis of which an abnormality caused at a terminal is determined;

DESCRIPTION OF THE PREFERRED EMBODIMENTS

Referring to the attached drawings, preferred embodiments of the present invention will be described.

Figure 1:
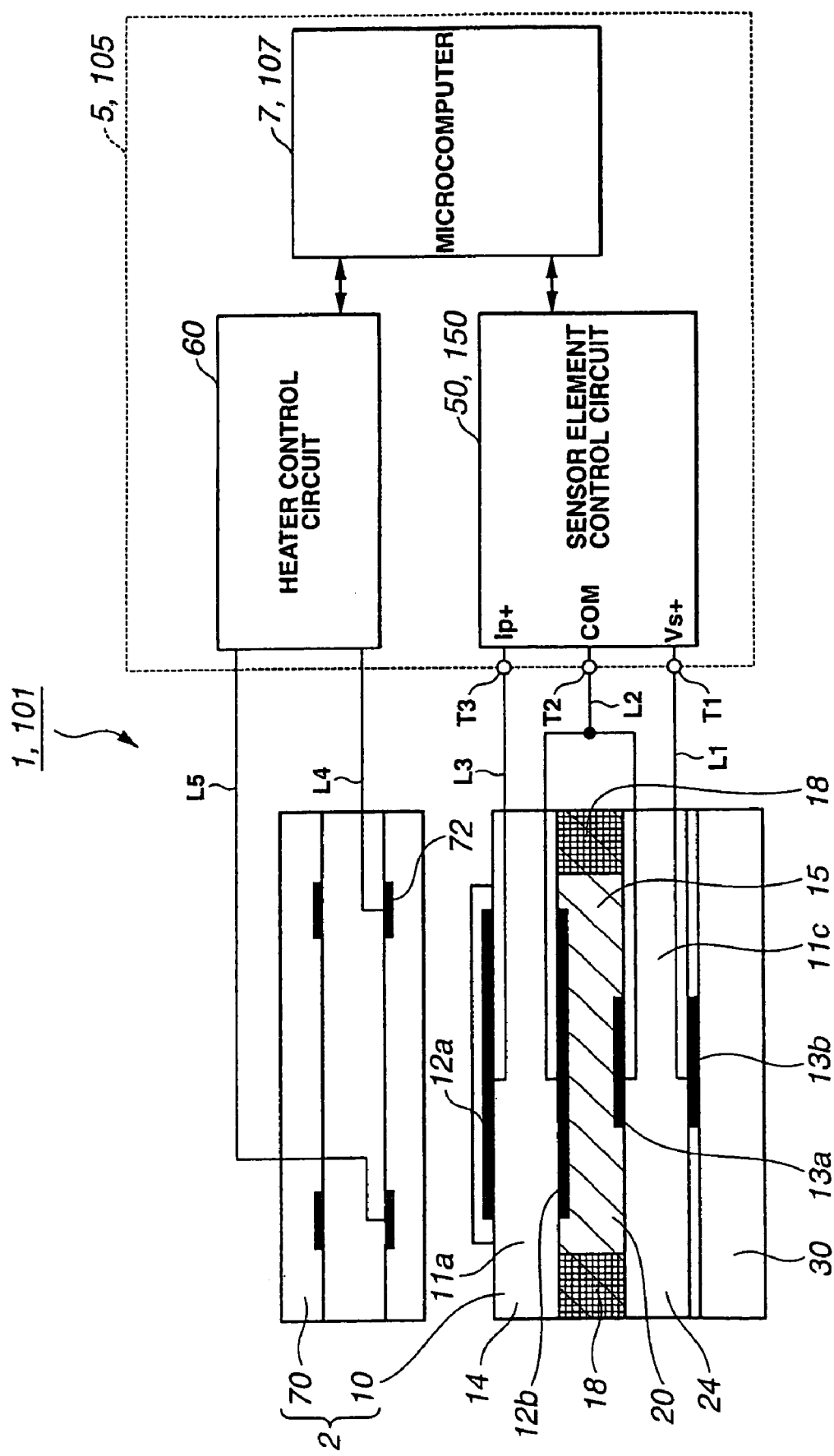
FIG. 1 is a schematic view of a gas concentration measuring device including an abnormality diagnosis apparatus therefor.

FIG. 1 shows a gas concentration measuring device 1 including an abnormality diagnosis apparatus according to an embodiment of the present invention. In the meantime, the gas concentration measuring device 1 of this embodiment is for measuring an oxygen concentration in an exhaust gas of an internal combustion engine.

As shown in FIG. 1, the gas concentration measuring device 1 of this embodiment includes a gas sensor 2 and an ECU (Electronic Control Unit) 5 electrically connected to the gas sensor 2 and has a function of measuring an oxygen concentration of a measured gas.

The gas sensor 2 includes a sensor element 10 for detecting a concentration of a measured gas, i.e., oxygen contained in an exhaust gas and a heater 70 for holding the sensor element 10 at an activation temperature.

The sensor element 10 is a wide-range air-fuel ratio sensor and includes a pump cell 14, an insulation layer 15, an oxygen concentration detecting cell or electromotive force cell 24 and a reinforcement plate 30 that are stacked or laminated in this order on upon another.

The pump cell 14 includes an oxygen ion conductive, solid electrolytic body 11a in the form of a thin plate and a pair of first pump electrode 12a and second pump electrode 12b disposed on front and rear surfaces of the solid electrolytic body 11a, respectively. Of the electrodes, the first pump electrode 12a is electrically connected with one end of a line L3. Further, the second pump electrode 12b is connected with one end of a line L2. In the meantime, the other ends of the lines L3, L2 are electrically connected to a third connecting terminal T3 and second connecting terminal T2, respectively.

The oxygen concentration detecting cell 24 includes, similarly to the pump cell 14, an oxygen ion conductive, solid electrolytic body 11c in the form of a thin plate and a pair of first detecting electrodes 13a and second detecting electrode 13b disposed on front and rear surfaces of the solid electrolytic body 11c. Of the detecting electrodes, the first detecting electrode 13a is electrically connected to the above-described second pump electrode 12b. Accordingly, to the one end of the line L2 is electrically connected the second pump electrode 12b and the first detecting electrode 13a. Further, to the second detecting electrode 13b is electrically connected one end of a line L1. In the meantime, the other end of the line L1 is electrically connected to a first connecting terminal T1 of the ECU 5.

In this connection, each of the solid electrolytic bodies 11a and 11c is made of a material containing zirconia as a major component. Further, the pump electrodes 12a, 12b and the detecting electrodes 13a, 13b are made of a material containing platinum as a major component so as to be porous.

The insulation layer 15 is disposed between the pump cell 14 and the oxygen concentration detecting cell 24 so as to electrically insulate therebetween. The insulating layer 15 is made of a material containing alumina as a major component.

Between the pump cell 14 and the oxygen concentration detecting cell 24 is formed a measurement chamber 20 surrounded by the insulating layer 15. The second pump electrode 12b of the pump cell 14 and the first detecting electrode 13a of the oxygen concentration detecting cell 24 are disposed so face the measurement chamber 20. In the meantime, the insulation layer 15 has at a portion thereof a porous diffusion layer (diffusion resistor) 18 that is communicated with a measured gas space or side and the measurement chamber 20 for introducing the measured gas component in the exhaust gas into the measurement chamber 20. The porous diffusion layer 18 causes the measured gas component to be diffused at a controlled speed into the measurement chamber 20 and is made of a material containing alumina as a major component so as to be porous.

The reinforcement plate 30 is disposed on a surface of the oxygen concentration detecting cell 24 on the side opposite to the measurement chamber 20 side so as to place the second detecting electrode 13b therebetween. By this, the strength of the entire sensor element 10 is attained.

Further, by the reinforcement plate 30, the second detecting electrode 13b of the oxygen concentration detecting cell 24 is shut off or isolated from the outside so that a closed space is formed around the second detecting electrode 13b. In the element structure described as above, a small constant current Icp is made to flow from the second detecting electrode 13b toward the first detecting electrode 13a, thereby pumping oxygen into the second detecting electrode 13b side. By this, oxygen of a predetermined concentration is stored in the closed space around the second detecting electrode 13b. For this reason, the second detecting electrode 13b is also called a self-generating reference electrode 13b.

In the meantime, the reinforcement plate 30 is nearly the same size as the solid electrolytic bodies 11a and 11c constituting the pump cell 14 and the oxygen concentration detecting cell 24, respectively and formed from a material containing ceramic as a major component into a plate-shape.

The heater 70 is in the form of a flat plate and disposed so as to oppose to the pump cell 14 of the sensor element 10. The heater 70 is made of a material containing alumina as a major component and has inside thereof a heater line 72 made of platinum. The heater 70 is controlled by a power supplied thereto from a heater control circuit 60 that will be described later so that the temperature of the sensor element 10 is within the range from 550 to 900° C. Further, to the opposite ends of the heater line 72 is connected one ends of the lines L4 and L5, respectively. In the meantime, the other ends of the lines L4 and L5 are electrically connected to a heater control circuit 60 of the ECU 5.

The ECU 5 consists of a sensor element control circuit 50 electrically connected to the sensor element 10 for controlling the same, the heater control circuit 60 electrically connected to the heater 70 for controlling the same and a microcomputer 7 for controlling the heater control circuit 60.

Of those components, the microcomputer 7 includes, though not shown, a central processing unit, RAM and ROM for storing data, programs, etc., and input and output ports for input and output of signals to and from outside circuits. In the microcomputer 7, commands such as operations and transfer of data are executed by programs stored in the RAM, etc. Further, in the microcomputer 7, the signals inputted to the input port is reflected on the content of an input port register and the content stored in an output port register is supplied as an output signal to the output port.

The sensor element control circuit 50 has a Vs+ terminal, COM terminal and Ip+ terminal. Those terminals are electrically connected to first to third terminals T1 to T3 of the ECU 5. Accordingly, the second detecting electrode 13b of the sensor element 10 is electrically connected to the Vs+ terminal by way of the line L1 and the first connecting terminal T1. Further, the second pump electrode 12b and the first detecting electrode 13a of the sensor element 10 are electrically connected to the COM terminal by way of the line L2 and the second connecting terminal T2. Further, the first plump electrode 12a of the sensor element 10 is electrically connected to the Ip+ terminal by way of the line L3 and the third connecting terminal T3.

In the sensor element 10, oxygen in the measured gas is diffused into the measurement chamber 20 by way of the porous diffusion layer 18 in accordance with the oxygen concentration of the measured gas. The sensor element 10 has such a characteristic as to generate, under the condition where the mixture supplied to the engine is maintained at a theoretical air-fuel ratio, an electromotive force of 450 mV at the oxygen concentration detecting cell 24 in accordance with the difference in the oxygen concentration between the measurement chamber 20 and the closed space around the second detecting electrode 13b, the oxygen concentration in the closed space serving as a reference oxygen concentration. Namely, an electromotive force of 450 mV is generated between the first detecting electrode 13a and the second detecting electrode 13b.

In the meantime, the oxygen concentration in the exhaust gas varies depending upon a variation of the air-fuel ratio of the mixture supplied to the engine. This causes a variation of the oxygen concentration of the atmosphere within the measurement chamber 20 of the sensor element 10. Thus, in the gas concentration measurement device 1 of this embodiment, the current Ip that flows through the pump cell 14 is controlled by the sensor element control circuit 50 that will be described later so that the potential difference between the first detecting electrode 13a and the second detecting electrode 13b is maintained at 450 mV. Namely, pumping of oxygen by the pump cell 14 is performed so that the atmosphere within the measurement chamber 20 becomes the same as that attained when the mixture of the theoretical air-fuel ratio is supplied to the engine. On the basis of the current Ip, the oxygen concentration of the measured gas is measured.

Figure 2:
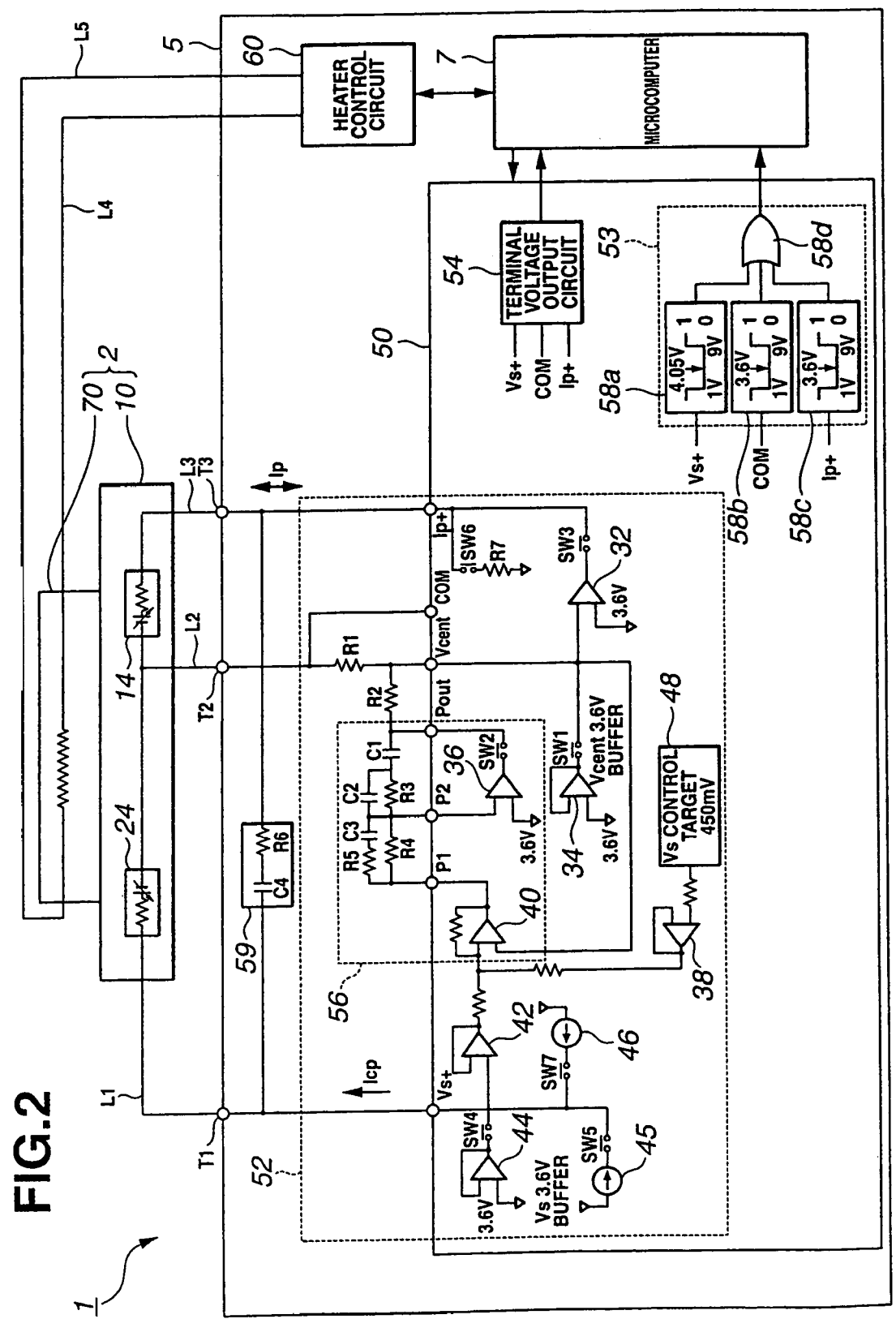
FIG. 2 is a circuit diagram of an electronic control unit of the gas concentration measuring device according to a first embodiment of the present invention.

Then, with reference to FIG. 2 the structure and operation of the ECU 5 will be described. FIG. 2 is a circuit diagram of an outline of the ECU 5.

As shown in FIG. 2, the ECU 5 consists of the sensor element control circuit 50 for controlling the sensor element 10, the heater control circuit 60 for controlling energization of the heater 70, and the microcomputer 7 for controlling the sensor element control circuit 50 and the heater control circuit 60.

The sensor element control circuit 50 consists of a sensor element drive circuit 52 for controlling an operation of the pump cell 14 and the oxygen concentration-detecting cell 24 that constitute the sensor element 10, an abnormal detecting circuit 53 that receives as an input the respective terminal voltages at the Vs+ terminal, COM terminal and Ip+ terminal that are the electrical connection points between the sensor element 10 and the sensor element drive circuit 52 and set an abnormal detection flag DIAG to 1 (DIAG=1) and supplies as an output a signal representative thereof to the microcomputer 7 when any of the terminal voltages supplied thereto becomes outside a predetermined range, and a terminal voltage output circuit 54 that supplies as an output the terminal voltages at the Vs+ terminal, COM terminal and Ip+ terminal to the microcomputer 7.

The sensor element drive circuit 52 includes an operation amplifier 32 for providing a current Ip that drives the pump cell 14, a PID control circuit 56 for improving the control characteristic of the Ip current, a constant current source 46 for providing a constant current Icp that flows through the oxygen concentration detecting cell 24 for maintaining the oxygen concentration at a self-generation reference electrode 13b constant, a constant current source 45 for supplying to the oxygen concentration detecting cell 24 a current larger than the constant current Icp supplied from the constant current source 46, a constant voltage source 48 for supplying a control target voltage of the Ip current, terminals, i.e., a Vs+ terminal, COM terminal and Ip+ terminal used for connecting the sensor element 10 to the sensor element drive circuit 52, terminals, i.e., a P1 terminal, P2 terminal and Pout terminal used for attaching thereto from the outside an element that determines the characteristics of the PID control circuit 56, and switches SW1 to SW7 for switching the operation mode of the sensor element drive circuit 52 in accordance with an operation mode selection signal supplied thereto from the microcomputer 7.

Of a pair of the pump electrodes constituting the pump cell 14, the first pump electrode 12a (refer to FIG. 1) is connected to the Ip+ terminal by way of the line L3 and the third connecting terminal T3. Further, the second pump electrode 12b (refer to FIG. 1) is connected to the COM terminal that provides a common reference voltage of the sensor element 10 by way of the line L2 and the second connecting terminal T2. In the meantime, the second pump electrode 12b is also connected to a Vcent terminal by way of the second connecting terminal T2 and a resistance element R1, in addition to the COM terminal. Further, of the pair of the detecting electrodes constituting the oxygen concentration detecting cell 24, the second detecting electrode 13b (refer to FIG. 1) is connected to the Vs+ terminal by way of the line L1 and the first connecting terminal T1, and the first detecting electrode 13a (refer to FIG. 1) is connected to the COM terminal by way of the line L2 and the second connecting terminal T2.

To the Ip+ terminal are connected the resistance element R7 and the operation amplifier 32. Of those, one end of the resistance element R7 is connected to the Ip+ terminal by way of the switch SW6 and the other end of the resistance element R7 is grounded. Further, the operation amplifier 32 has an inversion input terminal connected to the PID control circuit 56 by way of the resistance element R2 and a non-inversion input terminal to which a reference voltage of 3.6 V is applied. Further, the operation amplifier 32 has an output terminal connected to the Ip+ terminal by way of the switch SW3, thereby constituting a negative feedback circuit for controlling the sensor element 10.

To the COM terminal are connected the PID control circuit 56 and operation amplifiers 32 and 34. The PID control circuit 56 PID-calculates a deviation $\Delta Vs$ of the output voltage of the oxygen concentration detecting cell 24 from the control target voltage 450 mV and has a function of improving the control characteristics of the above-described negative feedback control. The PID control circuit 56 includes operation amplifiers 36 and 40, resistors R3 to R5 and capacitors C1 to C3, which are connected to the P1 terminal and the P2 terminal to determine the control characteristics of the PID control circuit 56. An input terminal of the PID control circuit 56 (i.e., the inversion input terminal of the operation amplifier 40) is connected to the Vs+ terminal by way of the operation amplifier 42 so that the output voltage Vs of the oxygen concentration detecting cell 24 is supplied as an input to the PID control circuit 56. Further the output terminal of the PID control circuit 56 is connected to the Pout terminal. The Pout terminal is connected to the Vcent terminal by way of the resistance element R2 and finally connected to the inversion input terminal of the operation amplifier 32. Further, the output terminal of the PID control circuit 56 is connected to the COM terminal by way of the resistance element R2 and the resistance element R1. In the meantime, the output of the PID control circuit 56 is ON/OFF controlled by means of the switch SW2.

The output of the constant voltage source 48 is supplied as an input to the inversion input terminal of the operation amplifier 40 by way of the operation amplifier 38. The constant voltage source 48 is a circuit for supplying 450 mV that is a control target voltage in control of the Ip current to the PID circuit 56 by way of the operation amplifier 40.

Further, the inversion input terminal of the operation amplifier 32 is connected to the COM terminal by way of the resistance element R1.

Further, to the Vcent terminal is connected the operation amplifier 34 by way of the switch SW1. The operation amplifier 34, as will be described later, is a circuit for supplying an abnormal determination current to the sensor element 10 for performing an abnormality diagnosis of the same.

To the Vs+ terminal are connected the constant current sources 45, 46 and the operation amplifiers 42, 44. Of those, the constant current source 46 is connected to the Vs+ terminal by way of the switch SW7. The constant current source 46 is a circuit for supplying the constant current Icp (e.g., 17 μA) that flows through the oxygen concentration detecting cell 24 in order to maintain the oxygen concentration of the atmosphere around the self-generation reference electrode 13b of the oxygen concentration detecting cell 24 constant. Further, the constant current source 45 is connected to the Vs+ terminal by way of the switch SW5. The constant current source 45, as will be described later, is a circuit for supplying, when a particular abnormality of the sensor element 10 is caused and thereafter the abnormality, is eliminated, a current (e.g., 100 μA) larger than the constant current Icp supplied from the constant current source 46 in order that the oxygen concentration of the atmosphere around the self-generation reference electrode 13b recovers rapidly. Further, the operation amplifier 44, similarly to the above-described operation amplifier 34 and as will be described later, is a circuit for supplying an abnormality determination current to the sensor element 10 for performing an abnormality diagnosis of the same. Further, the non-inversion input terminal of the operation amplifier 42 is connected to the Vs+ terminal.

In the meantime, between the Vs+ terminal and the Ip+ terminal is interposed an oscillation preventing circuit 59 consisting of a resistor R6 and a capacitor C4 for preventing oscillation of the sensor element drive circuit 52. Namely, the oscillation preventing circuit 59 constitutes an oscillation preventing means for preventing an oscillation phenomenon that is caused by a current control of an oxygen pump cell.

In the sensor element drive circuit 52 structured as described above, for measurement of the oxygen concentration of the measured gas, the switches SW2, S23 and SW7 are turned on and the switches SW1, SW4 to SW6 are turned off. In this instance, in case the measured gas results from excess supply of fuel (rich air-fuel ratio), the oxygen concentration of the gas within the measurement chamber 20 is lower than that resulting from a mixture of the theoretical air-fuel ratio, so that the output voltage Vs of the oxygen concentration detecting cell 24 becomes higher than 450 mV that is the control target voltage. Accordingly, there is caused a deviation $\Delta Vs$ of the output voltage Vs from the control target voltage, and the deviation $\Delta Vs$ is PID calculated by the PID control circuit 56 and fed back by means of the operation amplifier 32. Thus, the Ip current flows through the pump cell 14 to pump oxygen into the measurement chamber 20 by means of the pump cell 14 for making up the insufficiency of oxygen.

On the other hand, in case the measured gas results from insufficient supply of fuel (i.e., lean air-fuel ratio), the oxygen concentration of the gas within the measurement chamber 20 becomes higher than that resulting from a mixture of a theoretical air-fuel ratio, so that the Ip current flows through the pump cell 14 to pump the excess amount of oxygen out of the measurement chamber 20.

In this manner, the gas concentration measurement device 1 of this embodiment is capable of detecting the oxygen concentration in the measured gas through measurement of the Ip current that controls the pump cell 14 so that the output voltage Vs of the oxygen concentration detecting cell 24 becomes equal to 450 mV. In the meantime, the gas concentration measuring device 1 of this embodiment is configured so that the Ip current flowing through the pump cell 14 is voltage converted by means of the resistance element R2 and the voltage across the both terminals of the resistance element R2 (i.e., the voltage across the Vcent terminal and the Pout terminal) is supplied as an output to an input port of the microcomputer 7 by way of a differential amplifier circuit (not shown). Based on the oxygen concentration measured by the microcomputer 7, combustion control of the engine is finally performed.

The abnormality detecting circuit 53 consists of wind comparators 58a, 58b and 58c and an OR circuit 58d, and output terminals of the comparators 58a, 58b and 58c are connected in parallel to an input terminal of the OR circuit 58d. Though connecting lines are omitted in the figure, input terminals of the comparators are connected to the Vs+ terminal, COM terminal and Ip+ terminal, respectively.

The wind comparators 58a, 58b and 58c are configures to output low level signals when the terminal voltages at the Vs+ terminal, COM terminal and Ip+ terminal are within a predetermined voltage range and high level signals when the terminal voltages are outside the predetermined voltage range.

The terminal voltage at the Vs+ terminal is usually maintained at 4.05 V that is the sum of the reference voltage at the COM terminal, i.e., 3.6 V and the output voltage Vs of the oxygen concentration detecting cell 24, i.e., 450 mV. However, when the line L1 (also referred to as Vs+ line) or the like is shorted to the power source or the ground from some cause, the terminal voltage at the Vs+ terminal becomes the power source voltage or the ground level. Then, an excessively large abnormal current flows through the sensor element 10 to cause a possibility that the sensor element 10 is damaged. Thus, the wind comparator 58a is configured to compare the terminal voltage at the Vs+ terminal with a predetermined threshold value and outputs a high level signal when the terminal voltage at the Vs+ terminal exceeds the threshold value. Specifically, the upper limit of the threshold value is set at 9V or with consideration of a variation of the power source voltage of the sensor element control circuit 50, at a predetermined value that is obtained by subtracting a predetermined value (e.g., 1.5 V) from the power source voltage. The lower limit of the threshold value is set at 1V by consideration of floating up of the ground voltage level. When the terminal voltage at the Vs+ terminal rises beyond the upper limit of 9V or drops beyond the lower limit of 1V, the wind comparator 58a outputs a high level signal.

The terminal voltage at the COM terminal is usually controlled by the operation amplifier 32 so as to become equal to the reference voltage of 3.6 V. However, when the line L2 (also referred to as COM line) or the like is shorted to the power source voltage or the ground level from some cause, the terminal voltage at the COM terminal becomes equal to the power source potential or the ground potential similarly to the Vs+ terminal. Thus, the wind comparator 58b is configured to compare the terminal voltage at the COM terminal with a predetermined threshold value and output a high level signal when the terminal voltage at the COM terminal exceeds the threshold value. Specifically, similarly to the wind comparator 58a, the upper limit of the threshold value of the wind comparator 58b is set at 9V or a predetermined voltage and the lower limit is set at 1V. When the terminal voltage at the COM terminal rises beyond the upper limit of 9V or drops beyond the lower limit of 1V, the wind comparator 58b is configured to output a high level signal.

Also at the Ip+ terminal, when the line L3 (also referred to as Ip+ line) or the like is shorted to the power source voltage or the ground level from some cause, the terminal voltage at the Ip+ terminal becomes equal to the power source potential or the ground potential. Thus, the wind comparator 58c is configured to compare the terminal voltage at the Ip+ terminal with a predetermined threshold value and outputs a high level signal when the terminal voltage at the Ip+ terminal exceeds the threshold value. Specifically, in the wind comparator 58c to which the terminal voltage at the Ip+ terminal is inputted, the upper limit of the threshold value is set at 9V or a predetermined value and the lower limit is set at 1V so that the reference voltage of 3.6 V is intermediate between the upper and lower limits, similarly to the wind comparator 58b. When the terminal voltage at the Ip+ terminal rises beyond the upper limit of 9V or a predetermined voltage or drops beyond the lower limit of 1V, the wind comparator 58c is configured to output a high level signal.

The OR circuit 58d calculates the theoretical sum of the signals from the wind comparators 58a, 58b and 58c and set the abnormality detection flag DIAG to 1 (DIAG=1) and outputs a signal representative thereof.

In the meantime, when the terminal voltages at the Vs+ terminal, COM terminal and Ip+ terminal are within the predetermined voltage range, the abnormality detecting circuit 53 sets the abnormality detection flag DIAG to 0 (DIAG=0) and outputs a signal representative thereof to the microcomputer 7. In this manner, the abnormality detecting circuit 53 has a function of setting the abnormality detection flag DIAG to 1 (DIAG=1) when there occurs a short-circuit abnormality at any of the Vs+ line, COM line and Ip+ line to cause any of the terminal voltages at the Vs+ terminal, COM terminal and Ip+ terminal rises or drops beyond the threshold value (e.g., when an abnormality of the sensor element 10 is caused). In this connection, the wind comparators 58a, 58b and 58c constitute a determining means for determining whether a voltage at each of electrical connection points (i.e., Ip+ terminal, COM terminal and Vs+ terminal) is a predetermined abnormal voltage value.

The terminal voltage output circuit 54 is a circuit for outputting the terminal voltages at the Vs+ terminal, COM terminal and Ip+ terminal to the microcomputer 7 when the operation mode of the sensor element drive circuit 52 is an abnormality diagnosis mode which will be described later. In the meantime, though the connecting lines are omitted in the figure, the terminal voltage output circuit 54 has input terminals connected to the Vs+ terminal, COM terminal and Ip+ terminal, respectively.

The microcomputer 7 is connected to the sensor element drive circuit 52, abnormality detecting circuit 53 and terminal voltage output circuit 54. Specifically, a signal for switching an operation mode of the sensor element drive circuit 52 which will be described later (specifically, a signal for performing an ON/OFF control of the switches SW1 to SW7) is outputted from an output port of the microcomputer 7. The abnormality detection flag DIAG, the output signal of the terminal voltage output circuit 54 and the opposite end voltage of the resistance element R2 are inputted to the input port of the microcomputer 7. For this reason, the microcomputer 7 is capable of controlling the operation mode of the sensor element drive circuit 52 while being capable of determining whether an abnormality having been caused at the sensor element 10 continues and obtaining the terminal voltages at the respective terminals and a measurement value of an oxygen concentration of the measured gas. Further, the microcomputer 7 performs an abnormality diagnosis on the basis of the input signals from the abnormality detection circuit 53 and the terminal voltage output circuit 54. Further, the microcomputer 7 controls a heater control circuit 60 so that the temperature of the sensor element 10 is within the range from 550 to 900° C. In this connection, the microcomputer 7 constitutes a voltage detecting means and an abnormality diagnosis means.

The sensor element drive circuit 52 of this embodiment switches its operation mode into a gas concentration measurement mode, protection mode, abnormality diagnosis mode or reference oxygen recovery mode by ON/OFF controlling the switches SW1 to SW7.

The gas concentration measurement mode is an operation mode for performing a combustion control of the engine. The operation mode of the sensor element drive circuit 52 is switched to the gas concentration measurement mode when an abnormality of the sensor element 10 is not caused. In this operation mode, as shown in FIG. 3, the sensor element drive circuit 52 is operated so that the switches SW2, SW3 and SW7 are turned on and the switches SW1, SW4 to SW6 are turned off.

In this manner, when the switches SW2, SW3 and SW7 are turned on and the switches SW1 and SW4 to SW6 are turned off, as described above, the pump cell 14 is negative feedback controlled by the operation amplifier 32 by using the output voltage Vs of the oxygen concentration detecting cell 24 as a negative feedback voltage, and the oxygen concentration of the measured gas is measured by measuring the Ip current.

In the protection mode, when it is detected by the abnormality detecting circuit 53 that the terminal voltage at one of the Vs+ terminal, COM terminal and Ip+ terminal is outside a predetermined voltage range, all the outputs from the sensor element drive circuit 52 to the sensor element 10 are off (in other words, the sensor element drive circuit 52 is electrically shut off or separated from the sensor element 10), thereby protecting the sensor element 10.

In the protection mode, as shown in FIG. 3, all the switches SW1 to SW7 of the sensor element drive circuit 52 are off so that the signals inputted to the sensor element 10 from the operation amplifiers 32, 34, 36 and 44, and the constant current sources 45 and 46 are off, thus causing the sensor element 10 and the sensor element drive circuit 52 to be electrically shut off or separated from each other. Accordingly, an abnormal current does not continue flowing through the sensor element 10 to enable the sensor element 10 to be electrically protected. In this connection, the switches SW1 to SW7 constitute a shutting off means.

The abnormality diagnosis mode is an operation mode for performing upon occurrence of an abnormality of the sensor element 10 during driving of a vehicle, a diagnosis of determining the terminal at which the abnormality has occurred and a kind of the abnormality.

In the abnormality diagnosis mode, as shown in FIG. 3, the switches SW1, SW4 and SW6 are turned on and the switches SW2, SW3, SW5 and SW7 are turned off.

In this manner, since the switch SW3 is OFF, there is not any supply of current from the operation amplifier 32 to the pump cell 24. Further, since the switch SW2 is OFF, there is not any supply of current from the operation amplifier 35 to the pump cell 24. Thus, current control of the pump cell 14 is stopped. Accordingly, negative feedback control of the pump cell 14 is not performed.

Further, since the switches SW1, SW4 and SW6 are turned on, current is supplied from the operation amplifiers 34 and 44 to the pump cell 14 and the oxygen concentration detecting cell 24. In this connection, the operation amplifiers 34 and 44 constitute a current supply means.

To the microcomputer 7 are supplied the terminal voltages (also referred to as Vs+ voltage, COM voltage and Ip+ voltage) that are produced at the respective terminals (Vs+ terminal, COM terminal and Ip+ terminal) when current (hereinafter also referred to as abnormality determination current) provided by the operation amplifiers 34 and 44 flows through the cells 14 and 24. The microcomputer 7 compares the terminal voltages to determine which of the voltage conditions at the respective terminals fits which of the determination conditions shown in FIG. 4 and thereby determine the terminal at which an abnormality has occurred and the kind of the abnormality.

Specifically, when a short of any of the Vs+ line, COM line and Ip+ line to the ground potential (hereinafter referred to as a GND short) has been caused, it is determined that the Vs+ line has caused a GND short if the terminal voltages at the respective terminals has such a relation that the Vs+ voltage<the COM voltage and the Vs+ voltage<the Ip+ voltage, the Ip+ line has caused a GND short if the terminal voltages at the respective terminals has such a relation that the Ip+ voltage<the COM voltage and the Ip+ voltage<the Vs+ voltage, and the COM line has caused a GND short if the terminal voltages at the respective terminals has a relation other than those described above.

Further when a short of any of the Vs+ line, COM line and Ip+ line to the power source potential (hereinafter referred to as a VB short) has been caused, it is determined that the Vs+ line has caused a VB short if the terminal voltages at the respective terminals has such a relation that the Vs+ voltage>the COM voltage and the Vs+ voltage>the Ip+ voltage, the Ip+ line has caused a VB short if the terminal voltages at the respective terminals has such a relation that the Ip+ voltage>the COM voltage and the Ip+ voltage>the Vs+ voltage, and the COM line has caused a VB short if the terminal voltages at the respective terminals has a relation other than those described above.

Herein, the abnormality determination current provided by the operation amplifiers 34 and 37 is set at 5 mA or higher by consideration of the output voltages of the pump cell 14 and the oxygen concentration detecting cell 24 that vary depending up a variation of the oxygen concentration of the measured gas. The abnormality determination current is set so that the terminal voltages caused at the respective terminals when the terminals are supplied with the abnormality determination current are larger than the voltages produced by the pump cell 14 and the oxygen concentration detecting cell 24 in accordance with the oxygen concentration of the measured gas. By this, the abnormality diagnosis can be executed correctly.

In the meantime, when an abnormality diagnosis is performed by the abnormality diagnosis mode and thereafter the abnormality is dissolved or eliminated, the sensor element drive circuit 52 is switched into the gas concentration measurement mode to start measurement of the oxygen concentration of the measured gas. However in case the abnormality caused is the GND short at the Vs+ terminal, the VB short at the COM terminal or the VB short at the COM terminal, the oxygen concentration around the self-generation reference electrode 13b is lower than usual since at the abnormality diagnosis mode the current flows through the oxygen concentration detecting cell 24 in the direction to decrease the oxygen concentration around the self-generation reference electrode 13b. Under such a condition, when the operation mode of the sensor element drive circuit 52 is switched to the gas concentration measurement mode to start measurement of the oxygen concentration of the measured gas at once, it takes much time for the oxygen concentration around the self-generation reference electrode 13b becomes equal to a predetermined oxygen concentration since the constant current Icp supplied thereto from the constant current source 46 is a quite small current. For this reason, it takes a long time until the oxygen concentration can be measured correctly and accurately. Thus, the reference oxygen recovery mode is provided which makes the oxygen concentration around the self-generation reference electrode 13b recover rapidly by using the constant current source 45 that can supplies a larger current than the constant current source 46.

In this operation mode, the switches SW5 and SW6 are turned on and the switches SW1 to SW4 and SW7 are turned off. By this, a reference oxygen recovery current that is larger than the constant current Icp supplied by the constant current source 46 is supplied from the constant current source 45 to the oxygen concentration detecting cell 24, thus causing the oxygen concentration around the self-generation reference electrode 13b to recover rapidly. In this connection, the constant current source 45 constitutes an increased current supply means and the constant current source 46 constitutes a constant current supply means.

Then, with reference to FIGS. 5 and 6, a control process executed in the microcomputer 7 will be described.

Figure 5:
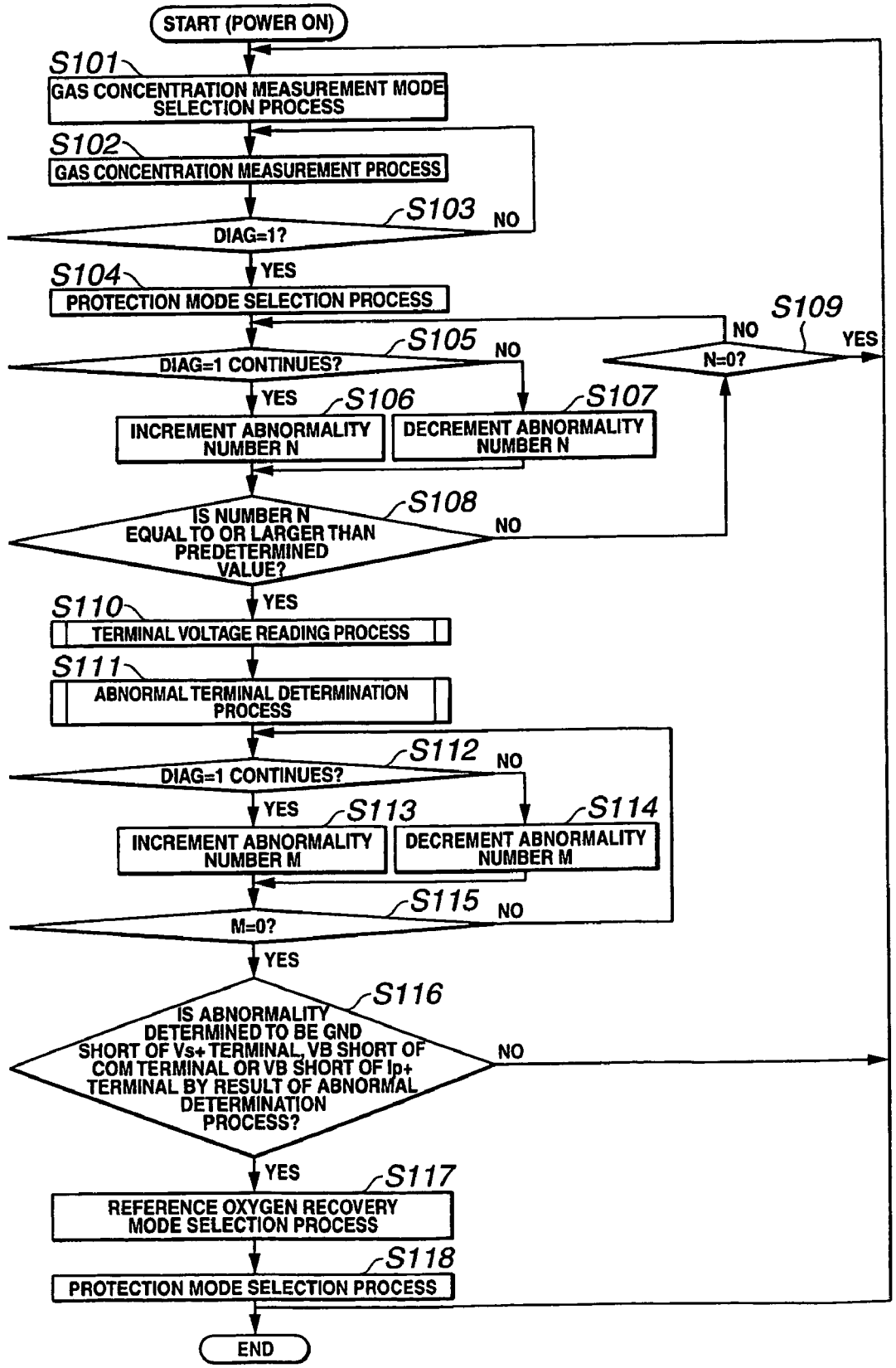
FIG. 5 is a flowchart of a main routine executed in a microcomputer of the electronic control unit.
Figure 6:
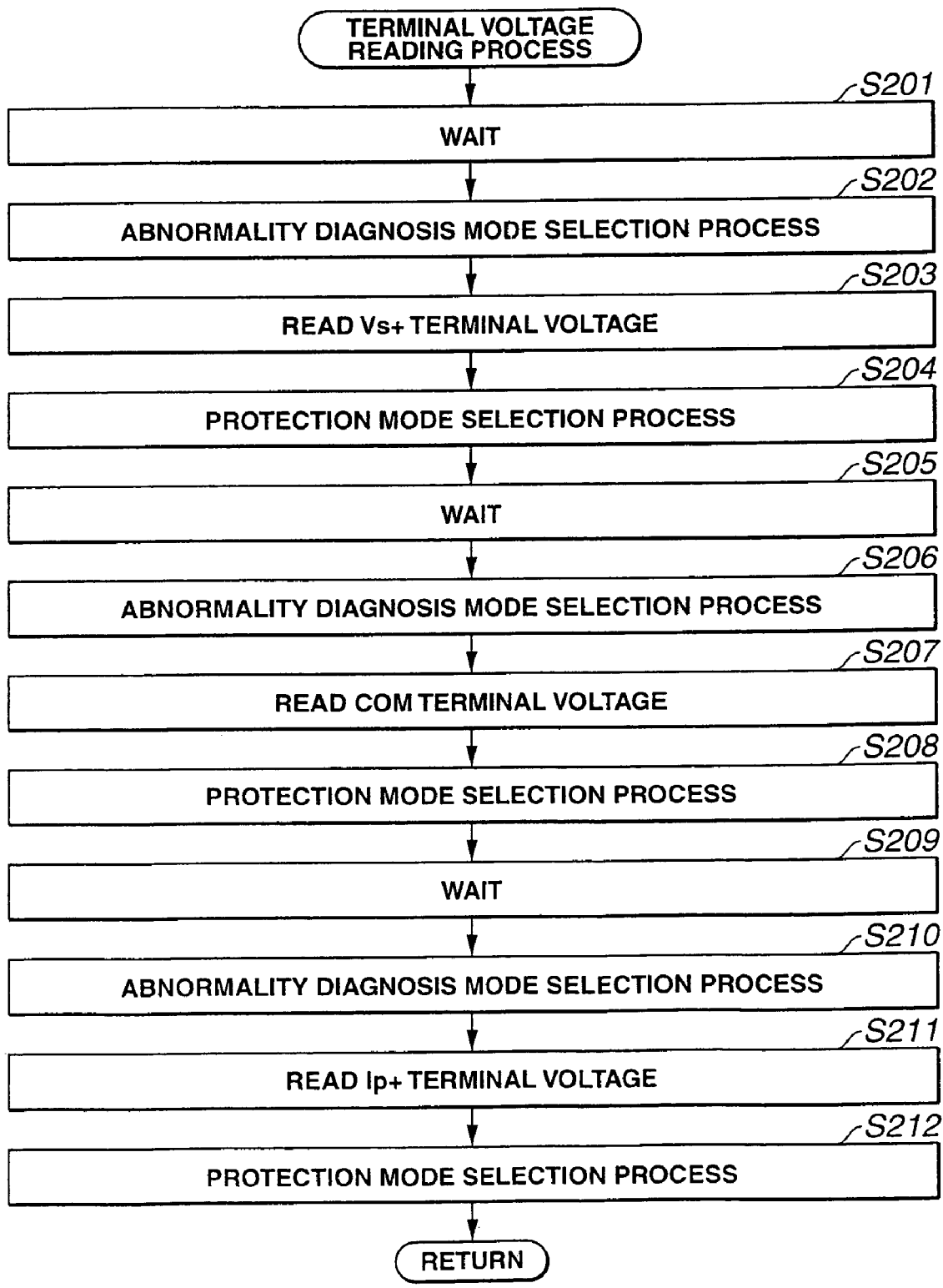
FIG. 6 is a flowchart of a subroutine executed in the microcomputer.

FIG. 5 is a flowchart showing a main routine executed in the microcomputer 7 and FIG. 6 is a flowchart showing a subroutine called up by the main routine.

As shown in FIG. 5, the process control by the microcomputer 7 is started by turning on a power source of an automotive vehicle. After the microcomputer 7 is initialized and the sensor element 10 is activated, the microcomputer 7 outputs to the sensor element drive circuit 52 a signal (gas concentration measurement mode selection signal) for switching the operation mode to a gas concentration measurement mode (S101). The sensor element drive circuit 52 is operated, when receiving a gas concentration measurement mode selection signal, so as to turn on the switches SW2, SW3 and SW7 and turn off the switches SW1, SW4 to SW6. By this, the operation mode of the sensor element drive circuit 52 is switched to the gas concentration measurement mode. Then, in step S102, a process of measuring an oxygen concentration in a measured gas is executed.

Then, in step S103, it is determined whether an abnormality detection flag DIAG outputted from the abnormality detection circuit 53 is 1 (i.e., DIAG=1). If not DIAG=1, i.e., if the terminal voltages of the sensor element 10 are within a predetermined voltage range (i.e., if there is not caused any abnormality in the sensor element 10), the control returns to step S102 to execute the process of measuring the oxygen concentration in the measured gas repeatedly.

On the other hand, if it is determined in step S103 that DIAG=1, the sensor element drive circuit 52 turns off the switches SW1 to SW7 so that the operation mode of the sensor element drive circuit 52 is switched to the protection mode (S104). By this, electrical connection between the sensor element 10 and the sensor element drive circuit 52 is shut off or separated to prevent an abnormal current from flowing through the sensor element 10 to damage the same.

Then, in step S105, it is determined whether it continues that DIAG=1. If it continues that DIAG=1, the program proceeds to step S106 to increment the abnormality number (i.e., the number of times of detecting an abnormality) N and the program proceeds to step S108. On the other hand, if it does not continue that DIAG=1, the program proceeds to step S107 to decrement the abnormality number N and the program proceeds to step S108.

In step S108, it is determined whether the abnormality number N is equal to or larger than a predetermined value. If the abnormality number N is equal to or larger than the predetermined value, it is determined that an abnormality has occurred in the sensor element 10 and the program proceeds to step S110. On the other hand, if the abnormality number N is not equal to or larger than the predetermined value, the program proceeds to step S109.

In step S109, it is determined whether the abnormality number N is equal to zero (i.e., N=0). If N=0, it is determined that an abnormality is eliminated or absent in the sensor element 10 and the program returns to step S101. Thereafter, the program proceeds to step S102 to execute the process of measuring the oxygen concentration in the measured gas repeatedly. On the other hand, if it is determined that the abnormality number N is not zero, the process steps from S105 to S108 are executed repeatedly.

Then, in step S110, a process of reading the terminal voltages is executed. The process of reading the terminal voltages will be described with reference to FIG. 6. In the process of reading the terminal voltages, firstly the microcomputer 7 waits a predetermined time (within a range from 100 ms to 1 sec., e.g., 1 sec) by using a timer (not shown) (S201). It is for the following reason to execute the process of making the microcomputer 7 wait a predetermined time. The sensor element drive circuit 52 is provided with the oscillation preventing circuit 59. For this reason, during a predetermined time after the operation mode of the sensor element drive circuit 52 is switched to the protection mode to thereby electrically shut off the sensor element 10 from the sensor element drive circuit 52, the terminal voltages at the terminals (Vs+ terminal, COM terminal and Ip+ terminal) become unstable transiently. Under such an unstable condition, correct terminal voltages at the terminals cannot be obtained. Thus, a process of waiting a predetermined time is executed until the terminal voltages at the terminals become stable. After lapse of a predetermined time, the program proceeds to step S202.

In step S202, the microcomputer 7 outputs to the sensor element drive circuit 52 a signal for switching the operation mode to the abnormality diagnosis mode (abnormality diagnosis mode selection signal). The sensor element drive circuit 52 is operated, when receiving the abnormality diagnosis mode selection signal, so as to turn on the switches SW1, SW4 and SW6 and turn off the switches SW2, SW3, SW5 and SW7. By this, the operation mode of the sensor element drive circuit 52 is switched to the abnormality diagnosis mode.

In step S203, the terminal voltage at the Vs+ terminal outputted from the terminal voltage output circuit 54 is read. In the meantime, the read terminal voltage at the Vs+ terminal is stored in the RAM (not shown) of the microcomputer 7.

In step S204, a signal for switching the operation mode to the protection mode (protection mode selection signal) is outputted to the sensor element drive circuit 52. The sensor element drive circuit 52 is operated, when receiving the protection mode selection signal, so as to turn off the switches SW1 to SW7. By this, the operation mode of the sensor element drive circuit 52 is switched to the protection mode.

In step S205, similarly to step S201, after waiting of a predetermined time, the program proceeds to step S206.

In step S206, similarly to step S202, the microcomputer 7 outputs the abnormality diagnosis mode selection signal to the sensor element drive circuit 52. The sensor element drive circuit 52 is operated, when receiving the abnormality diagnosis mode selection signal, so as to turn on the switches SW1, SW4 and SW6 and turns off the switches SW2, SW3, SW5 and SW7. By this, the operation mode of the sensor element drive circuit 52 is switched to the abnormality diagnosis mode.

In step S207, the terminal voltage at the COM terminal, that is outputted from the terminal voltage output circuit 54, is read. In the meantime, the read terminal voltage at the COM terminal is stored in the RAM (not shown) of the microcomputer 7.

In step S208, the microcomputer 7 outputs a protection mode selection signal to the sensor element drive circuit 52. The sensor element drive circuit 52 is operated, when receiving the protection mode selection signal, so as to turn off the switches SW1 to SW7. By this, the operation mode of the sensor element drive circuit 52 is switched to the protection mode.

In steps S209 to S212, the same processings as described above are executed. Namely, after waiting a predetermined time in step S209, the microcomputer 7 outputs, in step S210, an abnormality diagnosis selection signal to the sensor element drive circuit 52 to thereby switch the operation mode of the sensor element drive circuit 52 to the abnormality diagnosis mode. Thereafter, in step S211, the terminal voltage at the Ip+ terminal is read. In the meantime, the read Ip+ terminal voltage is stored in the RAM (not shown) of the microcomputer 7. Then, in step S212, the microcomputer 7 outputs a protection mode selection signal to the sensor element drive circuit 52 to thereby switch the operation mode of the sensor element drive circuit 52 to the protection mode.

Then, the program proceeds to an abnormal terminal determination process (S111) of the main flowchart in FIG. 5. In step S111, the terminal voltages read in steps S203, S207 and S211 and stored in the RAM of the microcomputer 7 are judged on the basis of determination conditions shown in FIG. 4 to determine the kind of the abnormality and the terminal at which the abnormality has occurred. In the meantime, the result of determination is stored in the RAM (not shown) of the microcomputer 7. By the abnormal terminal determination process, it is determined whether the abnormality of the sensor element 10 is a GND short or a VB short and which of the Vs+ terminal, COM terminal and Ip+ terminal is abnormal.

Then, in step S112, it is determined whether it continues that DIAG=1. If it continues that DIAG=1, the program proceeds to step S113 to increment the abnormality number (i.e., the number of times of detecting an abnormality) M and the program proceeds to step S115. On the other hand, if it does not continue that DIAG=1, the program proceeds to step S114 to decrement the abnormality number M and then proceeds to step S115.

In step S115, it is determined whether the abnormality number M is zero (i.e., M=0). If not M=0, the process steps S112 to S115 are executed repeatedly. On the other hand, if M=0, it is determined that the abnormality of the sensor element 10 is eliminated or absent and the program proceeds to step S116.

In step S116, the abnormal terminal determination result stored in the RAM of the microcomputer 7 in step S111 is read and it is determined whether the Vs+ terminal has caused a GND short, the COM terminal has caused a VB short or the Ip+ terminal has caused a VB short. If the abnormal terminal determination result does not meet with any one of the above-described determination conditions, the program proceeds to step S101. On the other hand, if the abnormal terminal determination result meets with one of the determination conditions, it is known that the oxygen concentration around the self-generation reference electrode 13b of the sensor element 10 is in a condition of being low since in the terminal voltage reading process in step S110 a current flows through the oxygen concentration detecting cell 24 in the direction to decrease the oxygen concentration around the self-generation reference electrode 13b. If under such a condition the operation mode of the sensor element drive circuit 52 is switched to the gas concentration measurement mode to execute measurement of the oxygen concentration at once, it takes much time until the oxygen concentration around the self-generation reference electrode 13b becomes equal to a predetermined value and therefore it takes much time until accurate measurement of the oxygen concentration can be attained.

Thus, if the answer in step S116 is affirmative, the program proceeds to step S117 to execute a reference oxygen recovery process.

In step S117, the microcomputer 7 outputs to the sensor element drive circuit 52 a signal for switching the operation mode to a reference oxygen recovery mode (a reference oxygen recovery mode selection signal). The sensor element drive circuit 52 is operated, when receiving the reference oxygen recovery mode selection signal, so as to turn on the switches SW5 and SW6 and turns off the switchers SW1 to SW4 and SW7. By this, to the oxygen concentration detecting cell 24 is supplied from the constant current source 45 in the same direction as the constant current Icp a reference oxygen recovery current of a large current value (e.g., 100 μA) for a predetermined time (e.g., 800 ms) so that the oxygen concentration around the self-generation reference electrode 13b is recovered rapidly.

Then, the program proceeds to step S118. In step S118, the microcomputer 7 outputs to the sensor element drive-circuit 52 a protection mode selection signal. The sensor element drive circuit 52 is operated, when receiving the protection mode selection signal, so as to turn off the switches SW1 to SW7. By this, the operation mode of the sensor element drive circuit 52 is switched to the protection mode. Thereafter, the program proceeds to step S101.

The above-described control is ended by turning off the power source of the automotive vehicle.

In this manner, the gas concentration measurement device 1 according to the first embodiment of the present invention detects whether an abnormal voltage is caused at the electrical connection points (Vs+ terminal, COM terminal, Ip+ terminal) between the sensor element 10 and the sensor element drive circuit 52 by means of the wind comparators 58a, 58b and 58c. If an abnormal voltage is caused at one of the electrical connection points, the operation mode of the sensor element drive circuit 52 is switched to the protection mode to thereby electrically shut off the sensor element 10 from the sensor element drive circuit 52. Accordingly, an abnormal current does not continue flowing through the sensor element 10, thus making it possible to prevent the sensor element 10 from being damaged by the abnormal current.

Further, the gas concentration measuring device 1 of this embodiment is configured so that an abnormality determination current that is necessary for abnormality diagnosis flows through the sensor element 10 for a predetermined time at the time of abnormality diagnosis of the sensor element 10 and is thereby capable of performing an abnormality diagnosis without damaging the sensor element 10.

Further, the gas concentration measuring device 1 of this embodiment is configured to supply to the oxygen concentration detecting cell 24, when it is determined by the result of abnormality diagnosis that a predetermined abnormality is caused at the sensor element 10 and thereafter the abnormality is eliminated, a reference oxygen recovery current that is larger than a usual current so that the oxygen concentration around the self-generation reference electrode 13b becomes equal to a predetermined oxygen concentration rapidly. Accordingly, it becomes possible to shorten the time necessary for the gas concentration measuring device 1 to become capable of measuring the oxygen concentration of the measured gas. Therefore, it becomes possible to restart combustion control of the engine rapidly.

With reference to FIGS. 1 and 7 to 10, a gas concentration measuring device 101 including an abnormality diagnosis apparatus according to a second embodiment of the present invention will be described.

The second embodiment is similar to the first embodiment so that like parts and portions will not be described again and only different portions will be described.

The gas concentration measuring device 101 of the second embodiment, similar to the gas concentration measuring device 1 in FIG. 1, includes a sensor element 10 for measuring the oxygen concentration of the measured gas in the exhaust gas, a sensor element control circuit 150 for controlling the sensor element 10, a heater 70 for holding the sensor element 10 at an activation temperature, a heater control circuit 60 for controlling the heater 70, and a microcomputer 107 for controlling the sensor element control circuit 150 and the heater control circuit 60.

In the meantime, the sensor element control circuit 150, heater control circuit 60 and microcomputer 107 constitute an electronic control unit 105.

Figure 7:
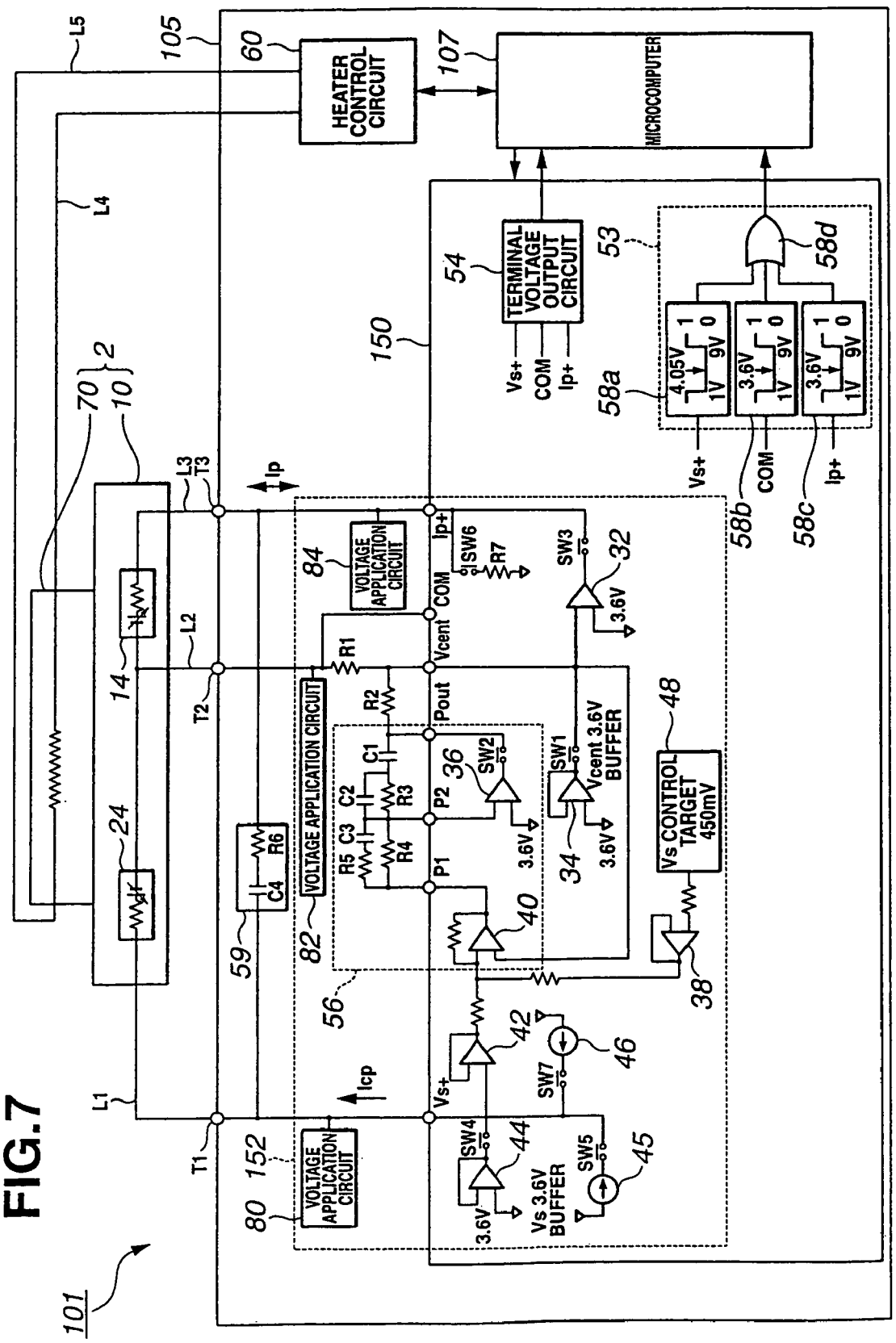
FIG. 7 is a circuit diagram of an electronic control unit of the gas concentration measuring device according to a second embodiment of the present invention.

Of the constituent parts described above, the sensor element 10, the heater 70 and the heater control unit 60 of the electronic control unit 105 are the same as those used in the first embodiment. Since the second embodiment differs from the first embodiment only in the sensor element control circuit 150 and the microcomputer 107 of the electronic control unit 105, description is made only to a different portion with reference to FIG. 7. FIG. 7 is a circuit diagram showing the electronic control unit 105.

As shown in FIG. 7, the sensor element control circuit 150 includes, similarly to the sensor element control circuit 50 of the first embodiment, a sensor element drive circuit 152 for controlling the pump cell 14 and the oxygen concentration detecting cell 24 that constitute the sensor element 10, an abnormality detecting circuit 53 that receives as an input the respective terminal voltages at the Vs+ terminal, COM terminal and Ip+ terminal that are the electrical connection points between the sensor element 10 and the sensor element drive circuit 152 and set an abnormal detection flag DIAG to 1 (DIAG=1) and outputs a signal representative thereof to the microcomputer 7 when one of the terminal voltages supplied thereto becomes outside of a predetermined range, and a terminal voltage output circuit 54 that outputs the terminal voltages at the Vs+ terminal, COM terminal and Ip+ terminal to the microcomputer 7. On the other hand, differing from the sensor element control circuit 50 of the first embodiment, the sensor element drive circuit 152 is added with voltage application circuits 80, 82 and 84 for applying an abnormality occurrence determination voltage to the Vs+ terminal, COM terminal and Ip+ terminal in order to finally determine occurrence of an abnormality after an abnormality of the sensor element 10 is detected and then confirmed by the abnormality detection circuit 53. In this connection, the voltage application circuits 80, 82 and 84 constitute a voltage application means.

The voltage application circuits 80, 82 and 84 will be described more in detail with reference to FIG. 8.

Figure 8:
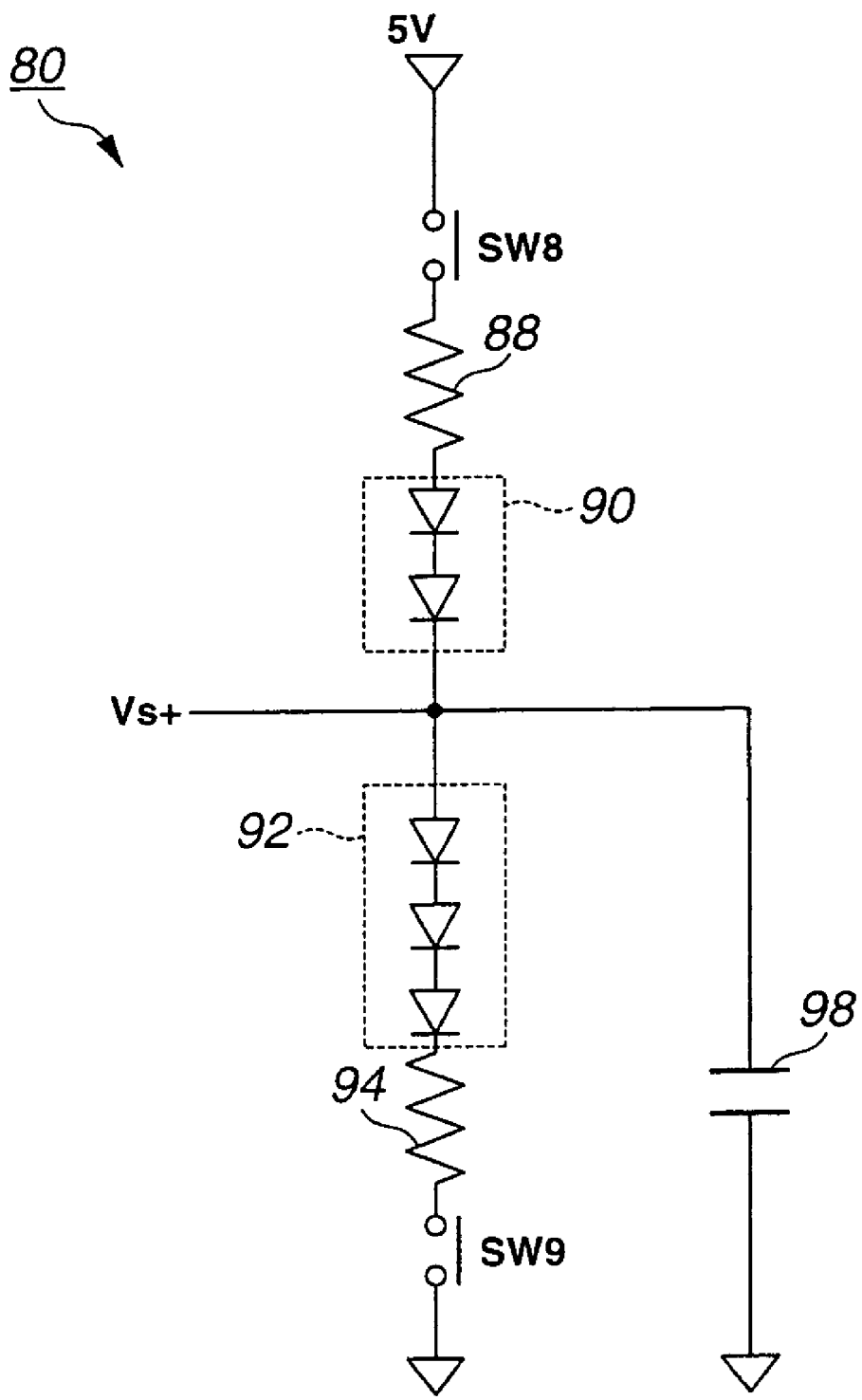
FIG. 8 is a circuit diagram of a voltage applying circuit.

FIG. 8 is a circuit diagram of the voltage application circuit 80 connected to the Vs+ terminal. As shown in FIG. 8, the voltage application circuit 80 includes two switches SW8 and SW9, two resistance elements 88 and 94, a plurality of diode circuits 90 and 92 and a capacitor 98. The switch SW8 is connected at one end to a power source of 5V and at the other end to an end of the resistance element 88. The other end of the resistance element 88 is connected to an anode terminal of the diode circuit 90 made up of two diodes connected in series.

To a cathode terminal of the diode circuit 90 is connected an anode terminal of the diode circuit 92 made up of three diodes connected in series. To a cathode terminal of the diode circuit 92 is connected an end of the resistance element 94. Further, to the other end of the resistance element 94 is connected an end of the switch SW9, the other end of the switch SW9 is grounded.

The capacitor 98 for removing noise is connected in parallel between the electrical connection point of the diode circuits 90, 92 and the ground potential.

The electrical connection point (output terminal) between the diode circuit 90 and the diode circuit 92 of the voltage application circuit 80 is connected to the Vs+ terminal.

In the meantime, the voltage application circuits 82 and 84 have the same circuit structure as the voltage application circuit 80 and each includes two switches SW8 and SW9, two resistance elements 88 and 94, a plurality of diode circuits 90 and 92 and the capacitor 98. Further, the output terminals of the voltage application circuits 82 and 84 are connected to the COM terminal and the Ip+ terminal, respectively.

Now, the difference of this embodiment from the first embodiment will be described. The gas concentration measuring device 1 of the first embodiment is configured to execute a process of making an abnormality diagnosis of the sensor element 10 when the abnormality detection circuit 53 detects that the voltage at one of the electrical connection points has become equal to an abnormal voltage value. However, even if an abnormality is caused in the sensor element 10, there is a case in which the abnormality is eliminated immediately thereafter. In such a case, if an abnormality diagnosis is performed immediately after the voltage at the electrical connection point has become equal to an abnormal voltage value and the measuring means is electrically separated from the electrical connection points, the abnormality diagnosis is performed though the gas sensor is normal and therefore an unnecessary process is performed. Furthermore, since an abnormality determination current is supplied to the sensor element 10 to perform the abnormality diagnosis, this means that a current is supplied through the sensor element 10 though the sensor element 10 is normal, thus causing a possibility that the gas sensor is deteriorated by unnecessary supply of current.

Thus, the gas concentration measuring device 101 of this embodiment is configured to switch the operation mode of the sensor element drive circuit 152 to a confirmation voltage application mode after the protection mode in order to confirm that an abnormality has occurred in the sensor element 10 and apply a confirmation voltage to the respective electrical connection points by means of the above-described voltage application means 80, 82 and 84. When the voltage at one of the electrical connection points becomes equal to an abnormal voltage value during the confirmation voltage application mode, the abnormality diagnosis is performed. In this manner, since the abnormality diagnosis is performed after it is confirmed that the sensor element 10 is abnormal, an abnormality diagnosis with respect to the sensor element 10 that is normal can be dispensed with, thus making it possible to prevent the gas concentration measuring device 101 from being lowered in the processing speed. Further, it becomes possible to eliminate unnecessary supply of current to the sensor element 10 that is normal and therefore suppress deterioration of the sensor element 10.

In the meantime, in the confirmation voltage application mode, the switches SW8 and SW9 of the voltage application circuits 80, 82 and 84 are turned on, and the voltage application circuits 80, 82 and 84 apply to the respective terminals a constant voltage that is determined by the power source of 5V, the resistance value of the resistance elements 88 and 94 and a voltage drop in the diode circuits 90 and 92. In this connection, by selecting the resistance value of the resistance elements 88 and 94 suitably, the current flowing through the respective cells 14 and 24 can be suppressed, thus making it possible to prevent deterioration of the cells 14 and 24 at the time of application of the confirmation voltage. Further, since the same voltage is applied to the respective terminals, it becomes possible to prevent the potential difference between the opposite ends of each of the cells 14 and 24 from becoming large, thus making it possible to prevent deterioration of the solid electrolytic bodies 11a and 11c.

Then, with reference to FIGS. 9 and 10, a process executed in the microcomputer 107 of the gas concentration determining device 101 having the sensor element control circuit 150 added with the voltage application circuits 80, 82 and 84 for application of the confirmation voltage will be described.

Figure 9:
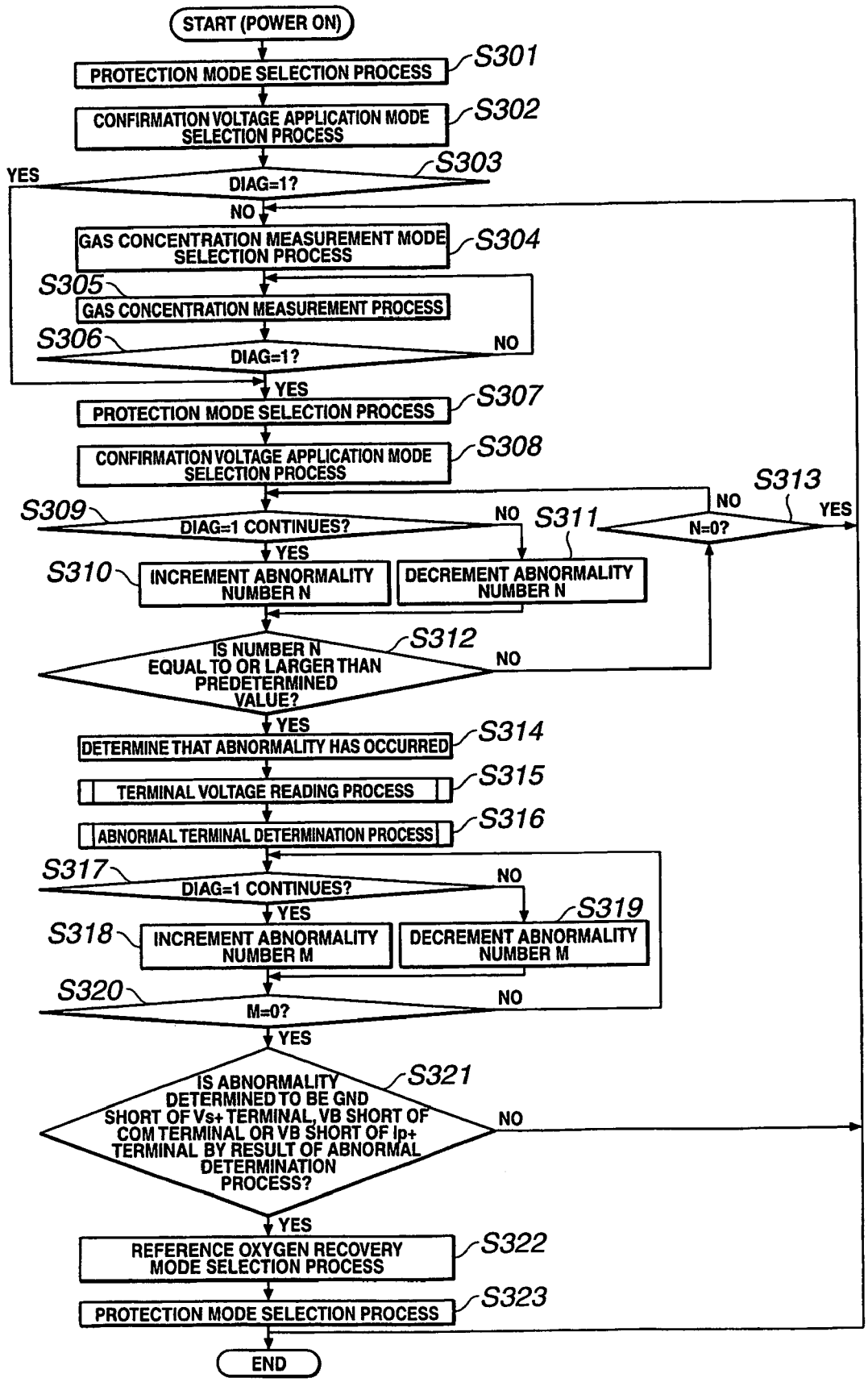
FIG. 9 is a flowchart of a main routine executed in the microcomputer of the electronic control unit of the second embodiment.
Figure 10:
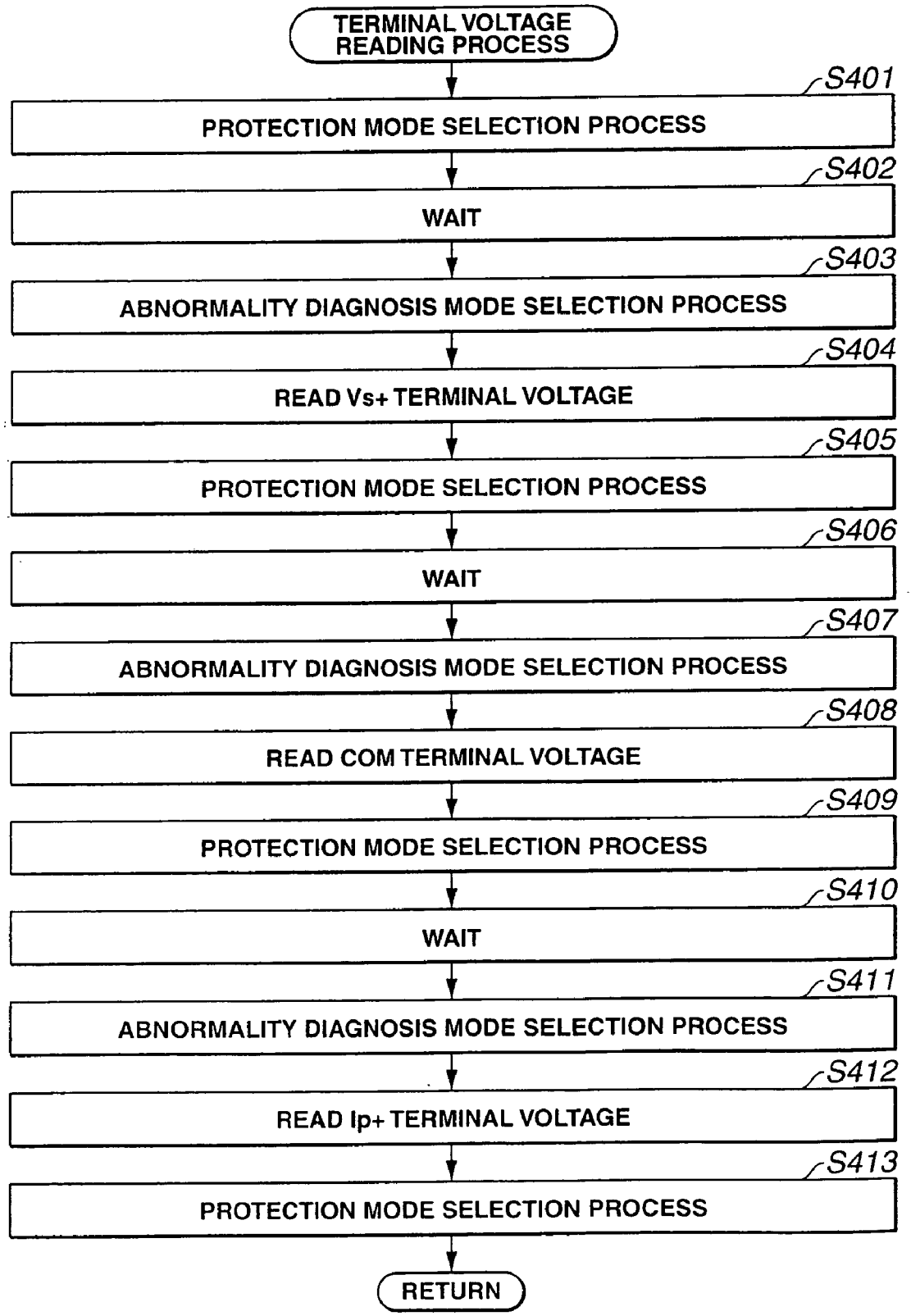
FIG. 10 is a flowchart of a subroutine executed in the microcomputer of the electronic control unit of the second embodiment.

FIG. 9 is a flowchart of a main routine executed in the microcomputer 107, and FIG. 10 is a flowchart of a sub-routine called for from the main routine.

As shown in FIG. 9, the microcomputer 107 starts the control process when the power of the automotive vehicle is turned on. The microcomputer 107, after initialized, outputs to the sensor element drive circuit 152 a protection mode selection signal (S301). The sensor drive circuit 152, when inputting the protecting mode selection signal, is operated to turn off the switches SW1 to SW9. By this, the operation mode of the sensor element drive circuit 152 is switched to the protection mode.

Then, in step S302, the microcomputer 107 outputs to the sensor element drive circuit 152 a signal for switching the operation mode to a confirmation voltage application mode (confirmation voltage application mode selection signal). The sensor element drive circuit 152, when inputting the confirmation voltage application mode selection signal, is operated so that the switches SW8 and SW9 are turned on. In the meantime, the switches SW1 to SW7 ate remained off. By this, the operation mode of the sensor element drive circuit 152 is switched to the confirmation voltage application mode.

Then, in step S303, it is determined whether the abnormality detection flag DIAG outputted from the abnormality detection circuit 53 is 1 (i.e., DIAG=1). If not DIAG=1, i.e., if the terminal voltages at the respective terminals of the sensor element 10 are within a predetermined voltage range (i.e., if an abnormality is not caused in the sensor element 10), the program proceeds to step S304. On the other hand, if DIAG=1, the program proceeds to step S307.

In step S304, the microcomputer 107 outputs a gas concentration measurement mode selection signal to the sensor element drive circuit 152. The sensor element drive circuit 152 is operated, when inputting the gas concentration measurement mode selection signal, so as to turn on the switches SW2, SW3 and SW7 and turn off the switches SW1, SW4 to SW6, SW8 and SW9. By this, the operation mode of the sensor element drive circuit 152 is switched to the gas concentration measurement mode. Then, in step S305, a process for measuring the oxygen concentration in the measured gas is executed. Then, in step S306, it is determined whether the measurement detection flag DIAG outputted from the abnormality detection circuit 53 is 1 (i.e., DIAG=1). If not DIAG=1, i.e., the terminal voltages of the sensor element 10 are within a predetermined voltage range (i.e., an abnormality is not caused in the sensor element 10), the program returns to step S305 to repeat the process of measuring the oxygen concentration in the measured gas. On the other hand, if DIAG=1, the program proceeds to step S307.

In step S307, the microcomputer 107 outputs a protection mode selection signal to the sensor element drive circuit 152. The sensor element drive circuit 152, when inputting the protection mode selection signal, is operated to turn off the switches SW1 to SW9. By this, the operation mode of the sensor element drive circuit 152 is switched to the protection mode.

Then, in step S308, the microcomputer 107 outputs a confirmation voltage application mode signal to the sensor element drive circuit 152. The sensor element drive circuit 152 is operated, when receiving the confirmation voltage application mode signal, so as to turn on the switches SW8 and SW9. In the meantime, the switches SW1 to SW7 remain off. By this, the operation mode of the sensor element drive circuit 152 is switched to the confirmation voltage application mode.

Then, in step S309, it is determined whether it continues that DIAG=1. If it continues that DIAG=1, the program proceeds to step S310 to increment the abnormality number N and the program proceeds to step S312. On the other hand, if it does not continue that DIAG=1, the program proceeds to step S311 to decrement the abnormality number N and the program proceeds to step S312.

In step S312, it is determined whether the abnormality number N is equal to or larger than a predetermined value. If the abnormality number N is equal to or larger than the predetermined value, the program proceeds to step S314 to determine that an abnormality has occurred in the sensor element 10. On the other hand, if the abnormality number N is less than the predetermined value, the program proceeds to step S313.

In step S313, it is determined whether the abnormality number N is zero (i.e., N=0). If N=0, it is determined that the abnormality on the sensor element 10 side as been eliminated or dissolved, and the program returns to step S304. Then, the program proceeds to step S305 to execute the process of measuring the oxygen concentration in the measured gas repeatedly. On the other hand, if it is determined in step S313 that the abnormality number N is not zero (i.e., not N=0), the process steps S309 to S313 are executed repeatedly.

Then, in step S315, a terminal voltage reading process is executed. The terminal voltage reading process will be described with reference to FIG. 10. Firstly, in the terminal voltage reading process, a protection mode selection signal is outputted to the sensor drive circuit 152 (S401). The sensor element drive circuit 152, when receiving the protection mode selection signal, is operated so as to turn off the switches SW1 to SW9. By this, the operation mode of the sensor element drive circuit 152 is switched to the protection mode. Then, in step S402, by using a timer (not shown) possessed by the microcomputer 107, a predetermined time (within a range from 100 ms to 1 sec, for example, 1 sec) is waited. The process of waiting the predetermined time is executed for the following reason. The sensor element drive circuit 152 is provided with an oscillation preventing circuit 59. For this reason, the terminal voltages at the respective terminals (Vs+ terminal, COM terminal and Ip+ terminal) becomes unstable transiently for a predetermined time after electrically shut off the sensor element 10 from the sensor element drive circuit 152. Under such an unstable condition, accurate voltage values at the respective terminals cannot be obtained. Thus, until the voltage values at the respective terminals become stable, the process of waiting a predetermined time is executed. After waiting of the predetermined time, the program proceeds to step S403.

In step S403, an abnormality diagnosis mode selection signal is outputted to the sensor element drive circuit 152. The sensor element drive circuit 152 is operated, when receiving the abnormality diagnosis mode selection signal, so as to turn on the switches SW1, SW4 and SW6 and turn off the switches SW2, SW3, SW5 and SW7 to SW9. By this, the operation mode of the sensor element drive circuit 152 is switched to the abnormality diagnosis mode.

In step S404, the terminal voltage at the Vs+ terminal is read. In the meantime, the read terminal voltage at the Vs+ terminal is stored in the RAM (not shown) of the microcomputer 107.

In step S405, a protection mode selection signal is outputted to the sensor element drive circuit 152. The sensor element drive circuit 152, when receiving the protection mode selection signal, is operated to turn off the switches SW1 to SW9. By this, the operation mode of the sensor element drive circuit 152 is switched to the protection mode.

In step S406, it is executed to wait a predetermined time similarly to step S402, and then the program proceeds to step S407.

In step S407, similarly to step S403, an abnormality diagnosis mode selection signal is outputted to the sensor element drive circuit 152. The sensor element drive circuit 152 is operated, when receiving the abnormality diagnosis mode selection signal, so as to turn on the switches SW1, SW4 and SW6 and turn off the switches SW2, SW3, SW5 and SW7 to SW9. By this, the operation mode of the sensor element drive circuit 152 is switched to the abnormality diagnosis mode.

In step S408, the terminal voltage at the COM terminal is read. In the meantime, the read terminal voltage at the COM terminal is stored in the RAM (not shown) of the microcomputer 107.

In step S409, the microcomputer 107 outputs a protection mode selection signal to the sensor element drive circuit 152. The sensor element drive circuit 152 is operated, when receiving the protection mode selection signal, so as to turn off the switches SW1 to SW9. By this, the operation mode of the sensor element drive circuit 152 is switched to the protection mode.

In steps S410 to S413, the same processings as described above are executed. Namely, in step S410, the program waits a predetermined time, and thereafter in step S411, an abnormality diagnosis mode selection signal is outputted to the sensor element drive circuit 152. Thereafter, in step S412, the terminal voltage at the Ip+ terminal is read. In the meantime, the read Ip+ terminal voltage is stored in the RAM (not shown) of the microcomputer 107. Then, in step S413, a protection mode selection signal is outputted to the sensor element drive circuit 152, thereby switching the operation mode of the sensor element drive circuit 152 to the protection mode.

Then, the control proceeds to the abnormal terminal determination process (S316) in the main flowchart of FIG. 9. In step S316, the respective terminal voltages read in the steps S404, S408 and S412 and stored in the RAM of the microcomputer 107 are judged on the basis of the determination conditions shown in FIG. 4 for thereby determining the kind of the abnormality and the terminal at which the abnormality is caused. In the meantime, the result of determination is stored in the RAM (not shown) of the microcomputer 107. By the abnormal terminal determination process, it is determined whether the abnormality caused in the sensor element 10 is the GND short or VB short and which of the Vs+ terminal, COM terminal and Ip+ terminal is abnormal.

Then, in step S317, it is determined whether it continues that DIAG=1. If it continues that DIAG=1, the program proceeds to step S318 to increment the abnormality number M, and the program proceeds to step S320. On the other hand, if it does not continue that DIAG=1, the program proceeds to step S319 to decrement the abnormality number M, and then proceeds to step S320.

In step S320, it is determined whether the abnormality number M is zero (i.e., M=0). If not M=0, the process steps S317 to S320 are executed repeatedly. On the other hand, if M=0, the it is determined that the abnormality of the sensor element 10 has been eliminated, and the program proceeds to step S321.

In step S321, the abnormal terminal determination result stored in the RAM of the microcomputer 107 is read and it is determined whether the Vs+ terminal caused the GND short, whether the COM terminal caused the VB short or whether the Ip+ terminal caused the VB short. If the abnormal terminal determination result does not meet with any of the determination conditions, the program proceeds to step S304. On the other hand, if the abnormal terminal determination result meets one of the determination conditions, it is known that a current flows through the oxygen concentration detecting cell 24 in the direction to decrease the oxygen concentration around the self-generation reference electrode 13b in the terminal voltage reading process in step S315, thus causing the oxygen concentration around the self-generation reference electrode 13b of the sensor element 10 to be low.

Thus, if the answer in step S321 is affirmative, the program proceeds to step S322 to execute the reference oxygen recovery process.

In step S322, a reference oxygen recovery mode selection signal is outputted to the sensor element drive circuit 152. The sensor element drive circuit 152 is operated, when receiving the reference oxygen recovery mode selection signal, so as to turn on the switches SW5 and SW6 and turn off the switches SW1 to SW4 and SW7 to SW9. By this, a reference oxygen recovery current of a large current value is supplied from the constant current source 45 to the oxygen concentration detecting cell 24 in the same direction as the constant current Icp for a predetermined time, thus causing the oxygen concentration around the self-generation reference electrode 13b to be recovered rapidly.

Then, the program proceeds to step S323. In step S323, a protection mode selection signal is outputted to the sensor element drive circuit 152. The sensor element drive circuit 152 is operated, when receiving the protection mode selection signal, so as to turn off the switches SW1 to SW9. By this, the operation mode of the sensor element drive circuit 152 is switched to the protection mode. Thereafter, the program returns to step S304.

The above-described control process is ended when the power of the automotive vehicle is turned off.

In this manner, in the gas concentration measuring device 101 of the second embodiment, the abnormality diagnosis is executed after the abnormality of the sensor element 10 is confirmed. Thus, it becomes possible to dispense with the abnormality diagnosis for the sensor element 10 that is normal and therefore prevent the process speed of the gas concentration measuring device 101 from being lowered. Further, it becomes possible to prevent unnecessary current from being supplied to the sensor element 10 to flow therethrough and thereby prevent the sensor element 10 from being deteriorated thereby.

In the meantime, when the operation mode of the sensor element drive circuit 152 is switched to the protection mode, there may possibly occur such a case in which the Vs+ terminal, COM terminal and Ip+ terminal present a high impedance, thus causing the terminal voltages at the respective terminals to be unstable (i.e., the input voltage of the abnormality detecting circuit 53 to be unstable) and therefore the detection of the abnormality condition to become inaccurate. In contrast to this, in the gas concentration measuring device 101 of the second embodiment, the confirmation voltage is applied to the respective terminals by means of the voltage application circuits 80, 82 and 84. Accordingly, the terminal voltages at the respective terminals do not become unstable, thus making it possible to detect the abnormality of the respective terminals (i.e., the abnormality of the sensor element 10) more assuredly.

Further, since the same voltage is applied to the respective terminals at the time of application of the confirmation voltage, it becomes possible to prevent deterioration of the sensor element 10.

The entire contents of Japanese Patent Application P2004-191722 (filed Jun. 29, 2004) are incorporated herein by reference.

Although the invention has been described above by reference to certain embodiments of the invention, the invention is not limited to the embodiments described above. Modifications and variations of the embodiment described above will occur to those skilled in the art, in light of the above teachings. For example, while in the above-described embodiments the sensor element 10 has been described as a wide range air-fuel ratio sensor, this is not for the purpose of limitation but the present invention may be applied to a NOx sensor having another cell in addition to the sensor element 10, i.e., having two measurement chambers. The scope of the invention is defined with reference to the following claims.

What is claimed is:

1. An abnormality diagnosis method for a gas concentration measuring device having a gas sensor and measurement means, the gas sensor having a measurement chamber in communication with a measured gas space and a pair of cells associated with the measurement chamber, the measurement means being electrically connected to the cells for measuring the concentration of a predetermined gas component of a measured gas in the measured gas space by controlling a current flowing through at least one of the cells, the abnormality diagnosis method comprising:

electrically shutting off the measurement means from the cells when a voltage at one of electrical connection points through which the measurement means is electrically connected to the cells becomes equal to a predetermined abnormal voltage value; and thereafter, electrically connecting the measurement means to the cells to perform an abnormality diagnosis of the gas sensor.

2. An abnormality diagnosis method according to claim 1, wherein the electrically connecting comprises supplying a predetermined current to the cells by way of the electrical connection points and performing the abnormality diagnosis on the basis of voltages at the respective electrical connection points that are detected at the time of supply of the predetermined current.

3. An abnormality diagnosis method according to claim 1, wherein the electrically connecting comprises applying a predetermined voltage to the electrical connection points, determining that the gas sensor is abnormal if one of voltages at the electrical connection points at the time of application of the predetermined voltage is the predetermined abnormal voltage value, and performing the abnormality diagnosis after it is determined that the gas sensor is abnormal.

4. An abnormality diagnosis method according to claim 1, wherein the measurement means is electrically connected with oscillation preventing means for preventing an oscillation phenomenon caused by a current control of one of the cells, and wherein the electrically connecting comprises performing the abnormality diagnosis after lapse of a predetermined time during which voltages at the respective electrical connection points are made unstable by the oscillation preventing means, after the measurement means is electrically shut off from the cells.

5. An abnormality diagnosis method according to claim 1, wherein the measurement means includes constant current supply means for supplying a constant current to the other of the cells in order to form a reference gas atmosphere, and wherein the electrically connecting comprises supplying to the other of the cells a current that flows in the same direction as the constant current and that is larger than the constant current when an abnormality is eliminated after it is once diagnosed by the abnormality diagnosis that there has occurred such an abnormality that a current flows through the other of the cells in the direction opposite to the constant current.

6. An abnormality diagnosis method for a gas concentration measuring device having a gas sensor and measurement means, the gas sensor having a measurement chamber in communication with a measured gas space by way of a diffusion resistor, an oxygen concentration detecting cell that produces a voltage in accordance with an oxygen concentration in the measurement chamber and an oxygen pump cell that pumps oxygen into or out of the measurement chamber in accordance with a current flowing therethrough, the oxygen concentration detecting cell having a solid electrolytic body and a pair of electrodes disposed in the solid electrolytic body, one of which electrodes faces the measurement chamber, the oxygen pump cell having a solid electrolytic body and a pair of electrodes disposed in the solid electrolytic body, one of which electrodes faces the measurement chamber, the measurement means being electrically connected to the oxygen concentration detecting cell and the oxygen pump cell for measuring the concentration of a predetermined gas component of a measured gas in the measured gas space by controlling a current flowing through the oxygen pump cell so that an output voltage of the oxygen concentration detecting cell is held at a constant value, the abnormality diagnosis method comprising:

electrically shutting off the measurement means from the oxygen concentration detecting cell and the oxygen pump cell of the gas sensor when a voltage at one of electrical connection points through which the measurement means is electrically connected to the oxygen concentration detecting cell and the oxygen pump cell of the gas sensor becomes equal to a predetermined abnormal voltage value; and thereafter, electrically connecting the measurement means to the oxygen concentration detecting cell and the oxygen pump cell of the gas sensor to perform an abnormality diagnosis of the gas sensor.

7. An abnormality diagnosis method according to claim 6, wherein the electrically connecting comprises supplying a predetermined current to the oxygen concentration detecting cell and the oxygen pump cell by way of the electrical connection points and performing the abnormality diagnosis on the basis of voltages at the respective electrical connection points that are detected at the time of supply of the predetermined current.

8. An abnormality diagnosis method according to claim 6, wherein the electrically connecting comprises applying a predetermined voltage to the electrical connection points, determining that the gas sensor is abnormal if one of voltages at the electrical connection points at the time of application of the predetermined voltage is a predetermined abnormal voltage value, and performing the abnormality diagnosis after it is determined that the gas sensor is abnormal.

9. An abnormality diagnosis method according to claim 6, wherein the measurement means is electrically connected with oscillation preventing means for preventing an oscillation phenomenon caused by a current control of the oxygen pump cell, and wherein the electrically connecting comprises performing the abnormality diagnosis after lapse of a predetermined time during which voltages at the respective electrical connection points are made unstable by the oscillation preventing means, after the measurement means is electrically shut off from the oxygen concentration detecting cell and the oxygen pump cell of the gas sensor.

10. An abnormality diagnosis method according to claim 6, wherein the other of the electrodes of the oxygen concentration detecting cell is disposed outside the measurement chamber and in a state of being shut off from the outside and the measurement means includes constant current supply means for supplying a constant current to the oxygen concentration detecting cell in order to form a reference oxygen atmosphere of a constant oxygen concentration around the other of the electrodes of the oxygen concentration detecting cell, and wherein the electrically connecting comprises supplying to the oxygen concentration detecting cell a current that flows in the same direction as the constant current and that is larger than the constant current when an abnormality is eliminated after it is once diagnosed by the abnormality diagnosis that there has occurred such an abnormality that a current flows through the oxygen concentration detecting cell in the direction opposite to the constant current.

11. An abnormality diagnosis apparatus for a gas concentration measuring device comprising:

a gas sensor having a measurement chamber in communication with a measured gas space and a pair of cells associated with the measurement chamber; and measurement means electrically connected to the cells for measuring the concentration of a predetermined gas component of a measured gas in the measured gas space by controlling a current flowing through at least one of the cells;

determining means for determining whether a voltage at one of electrical connection points through which the measurement means is electrically connected to the cells is a predetermined abnormal voltage value;

shut-off means for electrically shutting off the measurement means from the cells when it is determined by the determining means that a voltage at one of the electrical connection points is the predetermined abnormal voltage value; and abnormality diagnosis means for performing an abnormality diagnosis after the measurement means is electrically shut off from the cells by the shut-off mean.

12. An abnormality diagnosis apparatus according to claim 11, further comprising current supply means for supplying a predetermined current to the cells by way of the electrical connection points, and voltage detecting means for detecting voltages at the respective electrical connection points at the time of supply of the predetermined current by the current supply means, wherein the abnormality diagnosis means performs the abnormality diagnosis on the basis of voltages at the respective electrical connection points that are detected by the voltage detecting means.

13. An abnormality diagnosis apparatus according to claim 11, further comprising voltage application means for applying predetermined voltages to the respective electrical connection points after the measurement means is electrically shut off from the cells by the shut-off means, wherein the abnormality diagnosis means performs the abnormality diagnosis when it is determined by the determining means that a voltage at one of the electrical connection points is the predetermined abnormal voltage value at the time of application of the predetermined voltage by the voltage application means.

14. An abnormality diagnosis apparatus according to claim 11, wherein the voltage application means applies the same voltage to the respective electrical connection points.

15. An abnormality diagnosis apparatus according to claim 11, wherein the measurement means is electrically connected with an oscillation preventing means for preventing an oscillation phenomenon caused by a current control of one of the cells, and the abnormality diagnosis means performs the abnormality diagnosis after lapse of a predetermined time during which the voltages at the respective electrical connection points are made unstable by the oscillation preventing means, after the measurement means is electrically shut off from the cells by the shut-off means.

16. An abnormality diagnosis apparatus according to claim 11, wherein the measurement means further comprises constant current supply means for supplying a constant current to the other of the cells in order to form a reference gas component atmosphere of a constant concentration and increased current supply means for supplying to the other of the cells a current that flows in the same direction as the constant current and that is larger than the constant current when an abnormality is eliminated after it is once diagnosed by the abnormality diagnosis means that there has occurred such an abnormality that a current flows through the other of the cells in the direction opposite to the constant current.

17. An abnormality diagnosis apparatus for a gas concentration measuring device, comprising:

a gas sensor having a measurement chamber, an oxygen concentration detecting cell that produces a voltage in accordance with an oxygen concentration in the measurement chamber and an oxygen pump cell that pumps oxygen into or out of the measurement chamber in accordance with current flowing therethrough;

the measurement chamber being in communication with a measured gas space containing a measured gas by way of a diffusion resistor;

the oxygen concentration detecting cell having a solid electrolytic body and a pair of electrodes disposed in the solid electrolytic body, one of which electrodes faces the measurement chamber;

the oxygen pump cell having a solid electrolytic body and a pair of electrodes disposed in the solid electrolytic body, one of which electrodes faces the measurement chamber;

measurement means electrically connected to the oxygen concentration detecting cell and the oxygen pump cell for measuring the concentration of a predetermined gas component of the measured gas by controlling a current flowing through the oxygen pump cell so that an output voltage of the oxygen concentration detecting cell is maintained at a constant value;

determining means for determining whether a voltage at each of electrical connection points through which the measurement means is electrically connected to the oxygen concentration detecting cell and the oxygen pump cell is a predetermined abnormal voltage value;

shut-off means for electrically shutting off the measurement means from the oxygen concentration detecting cell and the oxygen pump cell when it is determined by the determining means that a voltage at one of the electrical connection points is the predetermined abnormal voltage value; and abnormality diagnosis means for performing an abnormality diagnosis after the measurement means is electrically shut off from the oxygen concentration detecting cell and the oxygen pump cell by the shut-off means.

18. An abnormality diagnosis apparatus according to claim 17, further comprising current supply means for supplying a predetermined current to the oxygen concentration detecting cell and the oxygen pump cell by way of the electrical connection points, and voltage detecting means for detecting voltages at the respective electrical connection points at the time of supply of the predetermined current by the current supply means, wherein the abnormality diagnosis means performs the abnormality diagnosis on the basis of voltages at the respective electrical connection points that are detected by the voltage detecting means.

19. An abnormality diagnosis apparatus according to claim 17, further comprising voltage application means for applying predetermined voltages to the respective electrical connection points after the measurement means is electrically shut off from the oxygen concentration detecting cell and the oxygen pump cell by the shut-off means, wherein the abnormality diagnosis means performs the abnormality diagnosis when it is determined by the determining means that a voltage at one of the electrical connection points is the predetermined abnormal voltage value at the time of application of the predetermined voltage by the voltage application means.

20. An abnormality diagnosis apparatus according to claim 17, wherein the voltage application means applies the same voltage to the respective electrical connection points.

21. An abnormality diagnosis apparatus according to claim 17, wherein the measurement means is electrically connected with an oscillation preventing means for preventing an oscillation phenomenon caused by a current control of the oxygen pump cell, and the abnormality diagnosis means performs the abnormality diagnosis after lapse of a predetermined time during which the voltages at the respective electrical connection points are made unstable by the oscillation preventing means, after the measurement means is electrically shut off from the oxygen concentration detecting cell and the oxygen pump cell by the shut-off means.

22. An abnormality diagnosis apparatus according to claim 17, wherein the other of the electrodes of the oxygen concentration detecting cell is disposed outside the measurement chamber and in a state of being shut off from the outside, and wherein the measurement means further comprises constant current supply means for supplying a constant current to the oxygen concentration detecting cell in order to form a reference oxygen atmosphere of a constant concentration around the other of the electrodes of the oxygen concentration detecting cell and increased current supply means for supplying to the oxygen concentration detecting cell a current that flows in the same direction as the constant current and that is larger than the constant current when an abnormality is eliminated after it is one diagnosed by the abnormality diagnosis means that there has occurred such an abnormality that a current flows through the oxygen concentration detecting cell in the direction opposite to the constant current.

* * * * *